(12) United States Patent
Robergé et al.

(10) Patent No.: US 7,155,447 B2
(45) Date of Patent: Dec. 26, 2006

(54) METHOD AND SYSTEM FOR GENERATION OF MEDICAL REPORTS FROM DATA IN A HIERARCHICALLY-ORGANIZED DATABASE

(75) Inventors: James Robergé, Darien, IL (US);
Jeffrey Soble, Highland Park, IL (US);
Alessandro Davide Donati, Chicago, IL (US)

(73) Assignee: Cyberpulse LLC, Highland Park, IL (US)

( * ) Notice: Subject to any disclaimer, the term of this patent is extended or adjusted under 35 U.S.C. 154(b) by 0 days.

(21) Appl. No.: 10/935,433

(22) Filed: Sep. 7, 2004

(65) Prior Publication Data

US 2005/0033773 A1 Feb. 10, 2005

Related U.S. Application Data

(63) Continuation of application No. 09/939,387, filed on Aug. 24, 2001, now Pat. No. 6,801,916, and a continuation-in-part of application No. 09/584,925, filed on May 31, 2000, now Pat. No. 6,381,611, which is a continuation of application No. 09/053,304, filed on Apr. 1, 1998, now Pat. No. 6,154,750.

(60) Provisional application No. 60/241,199, filed on Oct. 17, 2000.

(51) Int. Cl.
*G06F 17/30* (2006.01)

(52) U.S. Cl. .............................. 707/101; 707/1; 707/10; 345/419; 600/300

(58) Field of Classification Search ................ 707/101, 707/3; 600/300; 705/2, 3
See application file for complete search history.

(56) References Cited

U.S. PATENT DOCUMENTS

| | | | | |
|---|---|---|---|---|
| 6,154,750 A | * | 11/2000 | Roberge et al. | .......... 707/104.1 |
| 6,381,611 B1 | * | 4/2002 | Roberge et al. | .......... 707/104.1 |
| 6,801,916 B1 | * | 10/2004 | Roberge et al. | ............. 707/101 |
| 6,934,698 B1 | * | 8/2005 | Judd et al. | ..................... 707/1 |

* cited by examiner

*Primary Examiner*—Jean M. Corrielus
(74) *Attorney, Agent, or Firm*—Fitch, Even, Tabin & Flannery

(57) ABSTRACT

Methods, systems, and user interfaces for navigating hierarchical database views are provided, that support the efficient entry, review, and updating of data using a navigation display. At any point in the navigation process, the navigation display consists of buttons corresponding to nodes of hierarchical database data. Buttons form series of menu items representing nodes that lie along the path to the last node visited (the set of previously made choices) and the children of this node (the set of current choices). Other buttons act as placeholders to facilitate global movement within the database and when selected, initiate new series of menu items. Reports are generated by creating and formatting text based on data entered into the database. Other features are provided for increasing the efficiency of entering data and created reports from data in a hierarchical database views. Information is separated regarding the organization of the knowledge base and user interface from information from the data-entering step and associating the entered data items with sections used to organize information in the report.

20 Claims, 23 Drawing Sheets

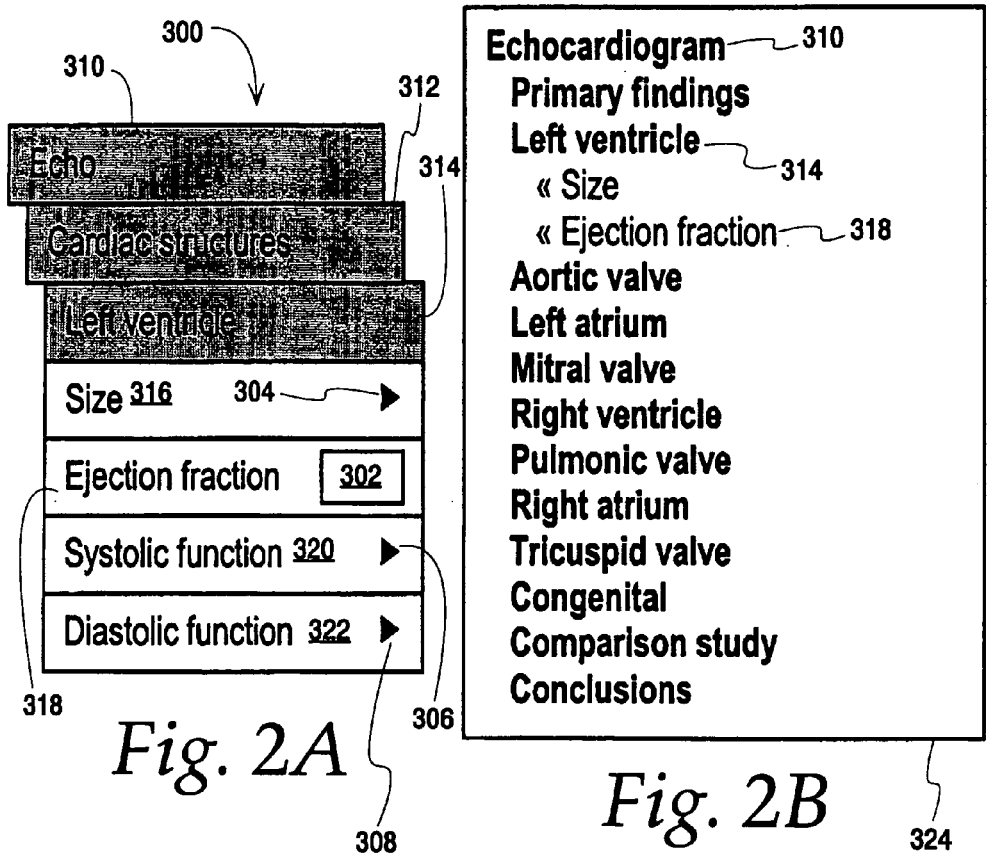
Fig. 2A
Fig. 2B
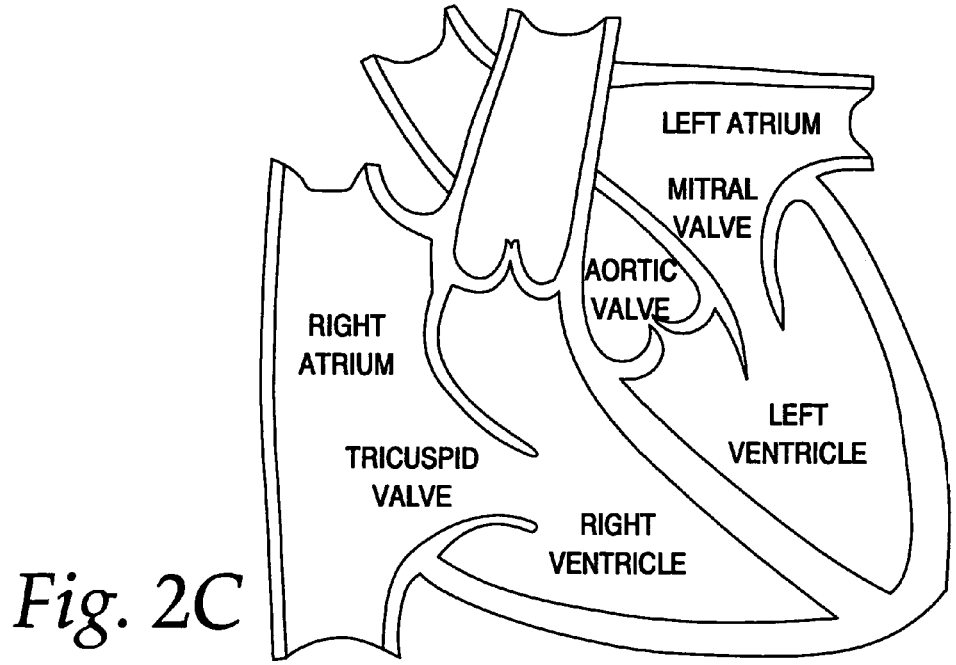
Fig. 2C

SELECTING A PLACEHOLDER SHORTCUT SYNCHRONIZES THE MENU SYSTEM TO THE CORRESPONDING NODE WITHIN TH KB HIERARCHY.

SELECTING A RECORDED FINDING WILL ALSO SYNCHRONIZE THE MENU SYTEM.

Fig. 3E

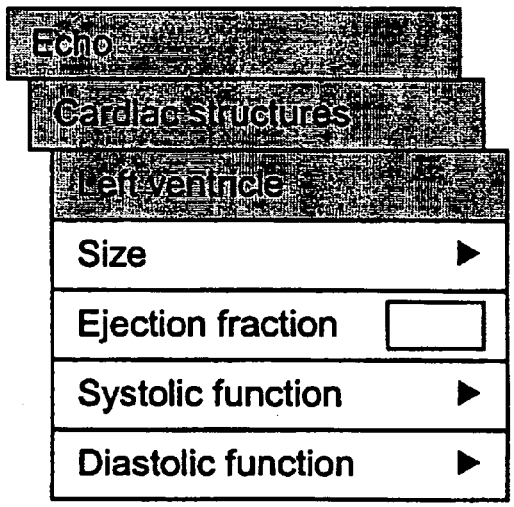

| Size | ▶ |
| Ejection fraction | ☐ |
| Systolic function | ▶ |
| Diastolic function | ▶ |

Fig. 3F

Echocardiogram
  Primary findings
    Left ventricle
      « Size
      « Ejection fraction
    Aortic valve
    Left atrium
    Mitral valve
    Right ventricle
    Pulmonic valve
    Right atrium
    Tricuspid valve
    Congenital
    Comparison study
    Conclusions

Fig. 3G

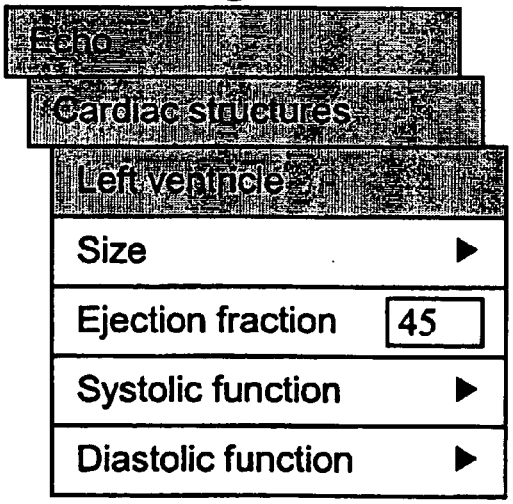

| Size | ▶ |
| Ejection fraction | 45 |
| Systolic function | ▶ |
| Diastolic function | ▶ |

Fig. 3H

Echocardiogram
  Primary findings
    Left ventricle
      « Size
      Ejection fraction: 45%
      « Systolic function
    Aortic valve
    Left atrium
    Mitral valve
    Right ventricle
    Pulmonic valve
    Right atrium
    Tricuspid valve
    Congenital
    Comparison study
    Conclusions

Cardiac structures
Left ventricle
Size

| Small |
| Normal |
| Dilated |

Primary findings: Left ventricular size was normal. Overall left ventricular systolic function was normal. Estimated left ventricular ejection fraction was in the range of 55% to 65%. There were no left ventricular regional wall motion abnormalities. Left ventricular wall thickness was normal.

---

Left ventricle: Left ventricular size was normal. Overall left ventricular systolic function was normal. Estimated left ventricular ejection fraction was in the range of 55% to 65%. There were no left ventricular regional wall motion abnormalities. Left ventricular wall thickness was normal.

Aortic valve: There was a normal appearing, trileaflet aortic valve. There was normal aortic valve leaflet excursion. Transaortic velocity was within the normal range. There was no evidence for aortic valve stenosis. There was no significant aortic valvular regurgitation.

Aorta: The aortic root was normal in size.

Mitral valve: Mitral valve structure was normal. There was normal mitral valve leaflet excursion. The transmitral velocity was within the normal range. There was no evidence for mitral stenosis. There was no significant mitral valvular regurgitation.

*Fig. 3J*

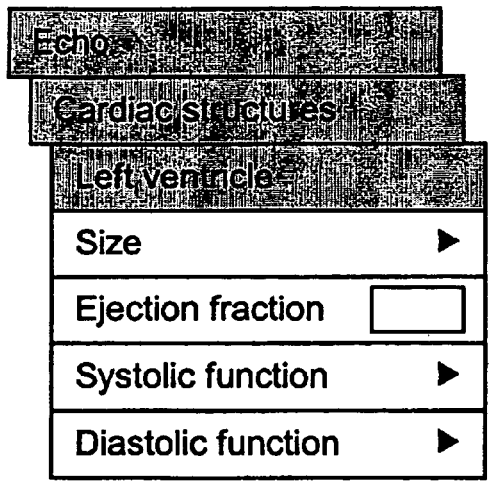
*Fig. 6A*
```
Echocardiogram
  Primary findings
  Left ventricle
    Normal LV size
    « Ejection fraction
    Normal LV systolic function
    Normal LV transmitral flow
    Normal LV pulmonary vein
    Normal LV diastolic function
  Aortic valve
  Left atrium
  Mitral valve
  Right ventricle
  Pulmonic valve
  Right atrium
```
*Fig. 6B*
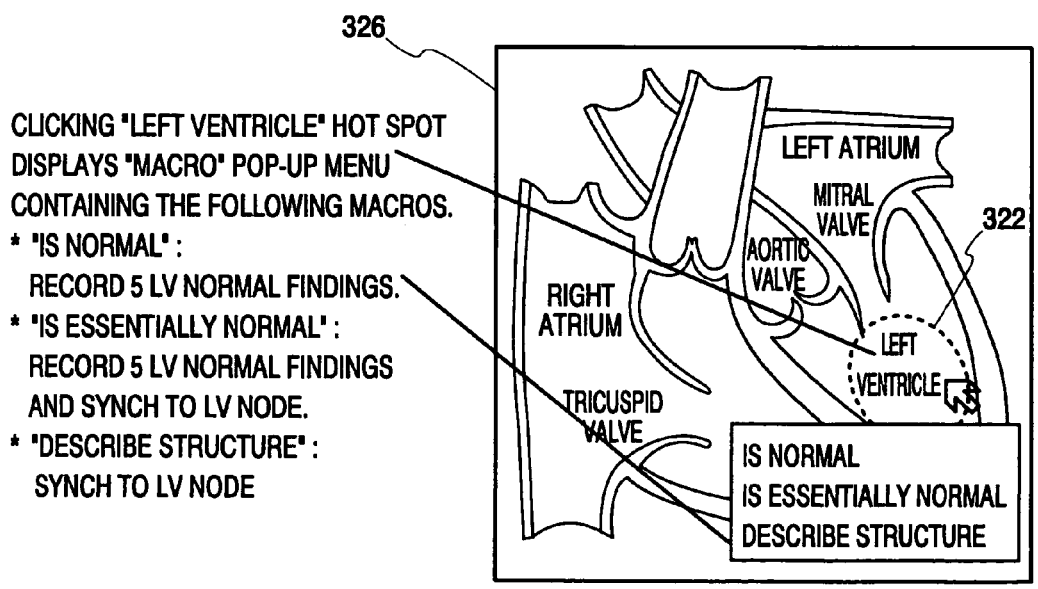
*Fig. 6C*

Primary findings: Left ventricular size was normal. Overall left ventricular systolic function was normal. Estimated left ventricular ejection fraction was in the range of 55% to 65%. There were no left ventricular regional wall motion abnormalities. Left ventricular wall thickness was normal.

Left ventricle: Left ventricular size was normal. Overall left ventricular systolic function was normal. Estimated left ventricular ejection fraction was in the range of 55% to 65%. There were no left ventricular regional wall motion abnormalities. Left ventricular wall thickness was normal.

Aortic valve: There was a normal appearing, trileaflet aortic valve. There was normal aortic valve leaflet excursion. Transaortic velocity was within the normal range. There was no evidence for aortic valve stenosis. There was no significant aortic valvular regurgitation.

Aorta: The aortic root was normal in size.

Mitral valve: Mitral valve structure was normal. There was normal mitral valve leaflet excursion. The transmitral velocity was within the normal range. There was no evidence for mitral stenosis. There was no significant mitral valvular regurgitation.

Left atrium: Left atrial size was normal.

Right ventricle: Right ventricular size was normal. Right ventricular systolic function was normal. Right ventricular wall thickness was normal.

Pulmonic valve: The structure of the pulmonic valve appears to be normal. The transpulmonic velocity was within the normal range. There was no pulmonic valve stenosis. There was no significant pulmonic regurgitation.

Pulmonary artery: The pulmonary artery was normal size. The estimated pulmonary artery systolic pressure was within the normal range.

Tricuspid valve: The tricuspid valve structure was normal. There was normal tricuspid leaflet excursion.

*Fig. 7A*

Primary findings: Left ventricular size was normal. Overall left ventricular systolic function was normal. Estimated left ventricular ejection fraction was in the range of 55% to 65%. There were no left ventricular regional wall motion abnormalities. Left ventricular wall thickness was normal.

Left ventricle: Left ventricular size was normal. Overall left ventricular systolic function was normal. Estimated left ventricular ejection fraction was in the range of 55% to 65%. There were no left ventricular regional wall motion abnormalities. Left ventricular wall thickness was normal.

Aortic valve: There was a normal appearing, trileaflet aortic valve. There was normal aortic valve leaflet excursion. Transaortic velocity was within the normal range. There was no evidence for aortic valve stenosis. There was no significant aortic valvular regurgitation.

Aorta: The aortic root was normal in size.

Mitral valve: Mitral valve structure was normal. There was normal mitral valve leaflet excursion. The transmitral velocity was within the normal range. There was no evidence for mitral stenosis. There was no significant mitral valvular regurgitation.

*Fig. 7B*

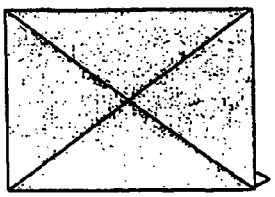 Cardiac Care Institute

*Fig. 8*

> St. Eligius Hospital
> 145 Revere Street, Boston, MA 12345
> Phone: 123-456-7890  Fax: 234-567-8901

---

> Donna Doe  123456789  Cardiac Catheterization  04-Jun-2000

| | | | | |
|---|---|---|---|---|
| MR#: | 123456789 | Height: | Location: | Lab |
| DOB: | 03-Dec-1931 | Weight: | | |

---

> Summary

1. An intervention (stent) was performed on the 75 % stenosis of the mid RCA. This was a successful intervention. There is no residual stenosis.

---

> Indications: Indication(s) for the cardiovascular procedures performed include: a significant coronary lesion in a major coronary artery. Medications: 9000 units of IV heparin were administered. Pre-procedural meds given: 8 mg of IV midazolam and 225 mcg of IV fentanyl. Medications given during the procedure: 200 mcg of intracoronary nitroglycerin.

> Cardiac hemodynamics Imported hemo tables

|    | Rest       | Phase 1     | Phase 2    | Phase 3    |
|----|------------|-------------|------------|------------|
| HR | 65         | 77          | 121        | 72         |
| Ao | 155/85(111)| 168/92(117) | 144/72(96) | 110/71(90) |
| LV | 155/8(68)  | 168/9(75)   | 144/7(58)  | 110/7(42)  |
| PA | 30/18(26)  | 28/19(24)   | 34/24(28)  | 31/24(27)  |
| RV | 30/5(15)   | 28/2(12)    | 34/6(17)   | 31/4(16)   |

---

> Vascular interventions First lesion summary An intervention (stent) was performed on the 75 % stenosis of the mid RCA. This was a successful intervention. There is no residual stenosis. Intervention detail:

> A SciMed Wiseguide 6Fr AL 1 FX guiding catheter was used to intubate the vessel. The lesion was crossed with a BMW .014 in x 180 cm wire.

*Fig. 9A*

```
Echocardiogram
  Primary findings
    Normal LV size
  Left ventricle
    Normal LV size  O
    « Ejection fraction
  Aortic valve
  Left atrium
  Mitral valve
  Right ventricle
  Pulmonic valve
  Right atrium
  Tricuspid valve
  Congenital
  Comparison study
  Conclusions
```

Primary findings: Left ventricular size was normal. Overall left ventricular systolic function was normal. Estimated left ventricular ejection fraction was in the range of 55% to 65%. There were no left ventricular regional wall motion abnormalities. Left ventricular wall thickness was normal.

Left ventricle: Left ventricular size was normal. Overall left ventricular systolic function was normal. Estimated left ventricular ejection fraction was in the range of 55% to 65%. There were no left ventricular regional wall motion abnormalities. Left ventricular wall thickness was normal.

Aortic valve: There was a normal appearing, trileaflet aortic valve. There was normal aortic valve leaflet excursion. Transaortic velocity was within the normal range. There was no evidence for aortic valve stenosis. There was no significant aortic valvular regurgitation.

Aorta: The aortic root was normal in size.

Mitral valve: Mitral valve structure was normal. There was normal mitral valve leaflet excursion. The transmitral velocity was within the normal range. There was no evidence for mitral stenosis. There was no significant mitral valvular regurgitation.

Fig. 12A

Primary findings: Left ventricular size was normal. Overall left ventricular systolic function was normal. Estimated left ventricular ejection fraction was in the range of 55% to 65%. There were no left ventricular regional wall motion abnormalities. Left ventricular wall thickness was normal.

Left ventricle: Left ventricular size was normal. Overall left ventricular systolic function was normal. Estimated left ventricular ejection fraction was in the range of 55% to 65%. There were no left ventricular regional wall motion abnormalities. Left ventricular wall thickness was normal.

Aortic valve: There was a normal appearing, trileaflet aortic valve. There was normal aortic valve leaflet excursion. Transaortic velocity was within the normal range. There was no evidence for aortic valve stenosis. There was no significant aortic valvular regurgitation.

Aorta: The aortic root was normal in size.

Mitral valve: Mitral valve structure was normal. There was normal mitral valve leaflet excursion. The transmitral velocity was within the normal range. There was no evidence for mitral stenosis. There was no significant mitral valvular regurgitation.

Fig. 12B

Primary findings: Left ventricular size was normal. Overall left ventricular systolic function was normal. Estimated left ventricular ejection fraction was in the range of 55% to 65%. There were no left ventricular regional wall motion abnormalities. Left ventricular wall thickness was normal.

Left ventricle: Left ventricular size was

| Left ventricle |
| --- |
| Size |
| Small |
| Normal |
| Dilated |

Aortic valve: There was a normal appearing, trileaflet aortic valve. There was normal aortic valve leaflet excursion. Transaortic velocity was within the normal range. There was no evidence for aortic valve stenosis. There was no significant aortic valvular regurgitation.

Aorta: The aortic root was normal in size.

Mitral valve: Mitral valve structure was normal. There was normal mitral valve leaflet excursion. The transmitral velocity was within the normal range. There was no evidence for mitral stenosis. There was no significant mitral valvular regurgitation.

QUICK REPORTS
Indications
Past history
Study information
Measurements
Left ventricle
  *Left ventricular size »
  *Systolic function »
  *Ejection fraction »
  Regional function
    Normal
    No diagnostic regional
    Cannot R/O regional
    Inadequate study
    Diffuse hypokinesis ▶
    Regional abnormal ▶
    Regional wall motion score
    Pseudoaneurysm ▶
  *Left ventricular wall thickness »
  *Left ventricular diastolic function »
  *LV measurements »
Aortic valve
Aorta
Mitral valve
Left atrium
Right ventricle
Pulmonic valve
Pulmonary artery
Tricuspid valve
Right atrium
Pericardium
Congenital heart disease

Fig. 15B

QUICK REPORTS
Indications
Past history
Study information
Measurements
Left ventricle
  Not well seen
  Normal
  * Size ▶
  * Systolic function ▶
  * Ejection fraction ▶
  * Thickness ▶
  Hypertrophy/obstruction ▶
  * Diastolic function ▶
  Thrombus/SEC/Mass ▶
  Septum ▶
  * Measurements ▶
Aortic valve
Aorta
Mitral valve
Left atrium
Right ventricle
Pulmonic valve
Pulmonary artery
Tricuspid valve
Right atrium
Pericardium
Congenital heart disease
Conclusions
Comparisons to previous

Fig. 16A

QUICK REPORTS
Indications
Past history
Study information
Measurements
Left ventricle
 Not well seen
 Normal
  Size ▶
   Normal left ventricular size
  Systolic function ▶
   Normal overall LV function
   * Ejection fraction ▶
  Regional function ▶
   No diagnostic regional wall motion abnormalities
  Thickness ▶
   Normal left ventricular wall thickness
  Hypertrophy/obstruction ▶
  * Diastolic function ▶
  Thrombus/SEC/Mass ▶
  Septum ▶
  * Measurements ▶
Aortic valve
Aorta
Mitral valve
Left atrium
Right ventricle
Pulmonic valve
Pulmonary artery
Tricuspid valve
Right atrium
Pericardium
Congenital heart disease

QUICK REPORTS
Indications
Past history
Study information
Measurements
Left ventricle
 Normal left ventricular size
 Normal overall LV function
 * Ejection fraction »
 Regional function
  No diagnostic regional wall motion abnormalities
  Regional WM (ASE)
   Lateral
    Basal
    Mid
    Apical
   All normal
   All hypokinetic
 Normal left ventricular wall thickness
 * Left ventricular diastolic function »
 * LV measurements »
Aortic valve
Aorta
Mitral valve
Left atrium
Right ventricle
Pulmonic valve
Pulmonary artery
Tricuspid valve
Right atrium
Pericardium
Congenital heart disease

450

```xml
<findingGroup heading="Left ventricle">
  <level>
    <finding phrase="Normal left ventricular size" />
    <finding phrase="Normal overall LV function" />
    <placeholder label="Ejection fraction" />
    <level heading="Regional function">
      <finding phrase="No diagnostic regional wall motion abnormalities" />
      <level heading="Regional WM (ASE)">
        <level heading="Lateral">
          <button label="Basal" pickList="true">
            <pickListEntry label="Normal" />
            <pickListEntry label="Hypo" />
            <pickListEntry label="Akinetic" />
            <pickListEntry label="Akin/scar" />
            <pickListEntry label="Dyskinetic "/>
            <pickListEntry label="Dys/scar" />
            <pickListEntry label="Aneurysm "/>
          </button>
          <button label="Mid" pickList="true"> ... </button>
          <button label="Apical" pickList="true"> ... </button>
          <button label="All normal" />
          <button label="All hypokinetic" />
        </level>
      </level>
    </level>
    <finding phrase="Normal left ventricular wall thickness" />
    <placeholder label="Left ventricular diastolic function" />
    <placeholder label="LV measurements" />
  </level>
</findingGroup>
```

METHOD AND SYSTEM FOR GENERATION OF MEDICAL REPORTS FROM DATA IN A HIERARCHICALLY-ORGANIZED DATABASE

CROSS-REFERENCE TO RELATED APPLICATIONS

This is a continuation division, continuation-in-part, of prior application Ser. No. 09/939,387, filed Aug. 24, 2001 now U.S. Pat. No. 6,801,916, which claims the benefit of U.S. Provisional Patent Application No. 60/241,199, filed Oct. 17, 2000, and is a CIP of U.S. patent application Ser. No. 09/584,925, filed May 31, 2000 now U.S. Pat. No. 6,381,611, which is a continuation of U.S. patent application No. 09/053,304, filed Apr. 1, 1998 now U.S. Pat. No. 6,154,750, which is hereby incorporated herein by reference in its entirety.

BACKGROUND OF THE INVENTION

1. Field of the Invention

This invention relates to methods for entry, update, and review of data in hierarchically-organized database views, and automated methods for generating medical reports.

2. Background of the Invention

One of the most challenging problems a software developer faces when designing a database system is creating a data entry mechanism that allows users to efficiently record information. In many environments, users operate under significant time pressures and are unwilling or unable to spend time on laborious data entry procedures. In order for a data entry mechanism to be effective, it must be fast, complete, and reconfigurable. In many cases, the data entry mechanism must also map onto small display screens or onto limited space within larger screens. This requirement has become increasingly important as more and more users take their computer systems with them as they move between work environments throughout the day. These highly mobile computing systems (e.g., hand-held computers) require data entry mechanisms that use screen space very economically. The same is true when data entry is performed within the context of screen-intensive imaging and graphics applications, e.g., when entering data while viewing digitized X-ray images.

Most existing database systems use a forms-based data entry mechanism. Unfortunately, forms-based techniques fail to satisfy the requirements listed above. Most databases include a large number of fields (categories) and elements. Since the number of fields that can be displayed on a form at any one time is very small, a user must navigate through multiple complex forms in order to enter data. In addition, forms-based systems are difficult, if not impossible, to reconfigure without programming.

Some existing database systems use data navigation mechanisms that are based on hierarchically-organized representations of the data. Note that we are discussing how the data is represented, not how the data is structured within the database. Hierarchical representations can be created for a variety of data structures (e.g., relational tables, hierarchical data structures, and network data structures).

One set of prior art techniques for navigating through hierarchically-organized database views is based on a diagrammatic representation of the hierarchy as a whole. In these techniques, a user moves around the hierarchy by selecting nodes on the diagram using a mouse or other pointing device. Since the hierarchy is very large, only those nodes that lie near the last node selected are displayed. The user can manually move the viewing window around (using scroll bars, for instance) and can reveal or hide levels of the hierarchy diagram by manually opening or closing nodes.

These techniques are designed to allow a user to view data elements in the context of the overall structure of the hierarchy and to visualize the logical relationships between data elements. However, the emphasis on overall structure makes these approaches ill-suited to the task of data entry. As the user moves down the hierarchy, he sees not only the nodes that represent possible choices for the next selection, but also large amounts of information that are irrelevant to the current data being entered. In addition, because much of the hierarchy diagram must, by necessity, be off-screen at any point in time, it is often difficult for the user to ascertain how he has reached a particular point in the hierarchy or how the displayed information fits within the overall structure.

A second set of prior art techniques for navigating through hierarchically-organized database views restrict navigation to movement up and down along the branches in the hierarchy. The contents of the levels that lie along the current branch are then displayed as cascading windows or menu lists. An example of this kind of system can be found in U.S. Pat. No. 5,715,449 to Peters et al., which discloses a browser tree structure for limiting how information is entered into a medical database. In the preferred mode, the system presents the person inputting the data with a limited number of choices of data to be entered, from which the operator selects specific phrases descriptive, for example, of the health care provider's observations or instructions. These techniques improve somewhat the ease with which a user can identify the current set of choices by placing possible candidates in the topmost window or rightmost list. However, these techniques are still unnecessarily wasteful of screen space. Much of the screen is cluttered with unselected choices at each of the levels that lie along the current branch. Equally important, navigation remains difficult because important navigational guides for moving back up the hierarchy, the nodes selected along the current path, for instance, are frequently hidden under a window or pushed off-screen entirely.

Also, present navigational techniques for hierarchical file directory structures that display the names of the files in a selected directory along with the path to that directory are limited to file selection, and do not address the entry or review of database information. Therefore, there remains a need for an easy to use interface, for entry, update, and review of data from a hierarchically-organized database view.

There is a particular need for such a system in the creation and management of medical records and the generation of reports from these records. For example, currently many medical reports are generated from transcription of a physician-dictated report. This procedure is inefficient and costly, since the process requires manual and inaccurate transcription. Furthermore, such a procedure is time-consuming to a physician, who must review and edit the transcribed report.

Attempts at solving this problem have focused on computer-based form systems. In these systems, a user enters information into a series of forms, to populate a database. These form-based systems have fundamental drawbacks. First, the systems are not flexible. Therefore, users cannot easily tailor the forms to their preferences. This poses serious issues in medical reporting, where physicians and medical institutions have specific preferences for their medical reports. Second, completing the forms is time consuming, as a user must go through and complete entries in many fields in the form. Therefore, there remains a need for an efficient, flexible, user-friendly interface for recording medical information and creating reports from the recorded information.

Finally, current medical records management systems do not provide an effective interface for formulating queries on recorded clinical data and generating reports from this data. Such a feature is important to physicians for medical accreditation purposes as well as for reviewing clinical data for scientific study. At best, existing query tools use some flavor of Query-By-Example (QBE) to form SQL queries on the underlying database. The principal failing of this approach when applied to the medical domain is that it forces the user to formulate a query in terms of the relationships that exist between data items in the database rather than in terms of the clinical relationships that naturally exist between the data items. Therefore, there remains a need for a query generation tool for medical data, which allows a query to be formed in an intuitive manner by taking advantage of the clinical relationships between data items, both to assist the user in locating data items and to express the relationship between these data items within the query itself.

The current invention meets these needs by providing an easy to use and flexible interface for the entry of medical information into a database, and generation of customized reports from that information. Furthermore, the current invention provides efficient and powerful methods for formulating queries on the resulting database using the interface and methods of the invention.

SUMMARY OF THE INVENTION

The current invention provides a set of integrated navigation, display generation, data entry, and data review methods, systems, and interfaces. These methods, systems, and interfaces work in concert to allow a user to move efficiently through a hierarchically-organized database view for the purpose of entering, reviewing, and updating data. Equally important, these methods produce a screen display that is highly economical in its use of screen real estate.

The current methods, systems, and interfaces provide a computer screen that is free of the clutter characteristic of existing techniques. In particular, the user does not see, and screen space is not wasted on, the display of unselected (and unselectable) choices. The user's ability to navigate the hierarchy is unhindered, however. At any point in the data entry and review process, the user can move back up the hierarchy (i.e., retrace her steps) simply by reselecting a button corresponding to a previously made choice or move down the hierarchy by selecting a button from among the current set of choices.

These methods, systems, and interfaces do not simply support the navigation of static data structures. A hierarchical database view contains multiple instances of various subhierarchies. The methods, systems, and interfaces of the present invention seamlessly blend the selection of subhierarchy instances (e.g., echocardiographic reports) into the navigation process and display outlined above. In other words, these methods, systems, and interfaces support navigation of both the structural and the temporal components of a database.

Nor are these methods, systems, and interfaces limited to use with hierarchical views in which each entry in the database corresponds to a single node in the hierarchy. Such views can easily become quite large and unwieldy (both for the database system and the user). The methods, systems, and interfaces of the present invention support hierarchical views in which the values assigned to several nodes combine to define a single database entry. The user simply inputs values for the nodes and the database entry is automatically constructed and stored.

Furthermore, the methods, systems, and interfaces of the present invention are not limited to marked/unmarked (i.e., yes/no) data items. The preferred embodiment of the present invention, for example, supports a diverse set of data types including numbers, text strings, dates, prescription doses, file names, Universal Resource Locators (URLs), and free-text comments. All of these data types may be input and reviewed within the context of the hierarchical navigation process and display outlined above.

In one aspect, the current invention provides an automated method for generating a medical report based on results of a medical examination of a patient. In another aspect, the current invention provides a medical report generating system for the automated generation of a medical report based on a medical examination of a patient. In another aspect the current invention provides a method for populating a database, preferably a medical information database. These methods and systems include or provide a hierarchically-organized database representation of a database, preferably a medical information database. The hierarchically-organized database representation includes a plurality of nodes capable of having further related nodes, fields, or attributes.

Furthermore, the methods and systems involve a user interface displaying the following:

1) a first series of menu items representing a first series of nodes according to their position in the hierarchical database view; and
2) a first series of shortcuts representing a second series of nodes in an arrangement facilitating global navigation of the hierarchical database view;
3) a second series of menu items that replace the first series of menu items when a shortcut is selected. The second series of menu items represent a third series of nodes according to their position in the hierarchical database view; and
4) a first series of placeholders for providing prompts for commonly entered information.

Placeholders are shortcuts that are required by the user. Shortcuts are items displayed in the summary viewer that mark areas of the tree that a user typically goes or wants to go. Also, such shortcuts allow for quick and easy navigation to that part of the tree allowing the user to enter data. Thus, all placeholders are shortcuts, but not all shortcuts are placeholders.

In the methods of the current invention, data is entered, based on results of a medical examination, into the hierarchically-organized database view by selecting a menu item or entering data into the menu item. Medical reports are generated by electronically transferring data from the hierarchically-organized database view into a report-generating function. Data entered into the hierarchically-organized database representation is electronically transferring data to the medical information database.

In preferred embodiments of the methods and systems of the current invention, the user interface further displays a graphical representation of an anatomical region of the patient or other information related to the medical report. In these embodiments, the graphical representation comprises a series of user-selectable portions effective for changing the series of menu items upon selection by a user.

The series of menu items and the series of shortcuts may be displayed within visually separated portions of the user interface, or may be displayed combined in one area on the user interface. The menu system and summary viewer may either be in two separate pieces or combined into a single space on the screen. In addition to the shortcuts described above, the summary viewer also facilitates a graphical user interface for the items found in the menu.

The methods, systems, and interfaces of the current invention, in certain preferred aspects, provide one or more of a series of additional functionalities that increase the efficiency and power of database entry, searching, and report generation, especially with respect to medical reports. These additional functionalities include the following:

1) functions that automatically copy data into multiple related portions of the database, and/or automatically prompt a user to enter data in related database fields;
2) automatic entry of certain data into Primary Findings sections of associated medical records; and
3) automatic customizable menus containing lists of items derived from information (e.g., particular product numbers of items in inventory) contained in a database maintained separately from the medical records database.

Finally, the current invention provides a query function using the user interface of the current invention. This is extremely valuable, as it provides a clinical context when creating queries, and powerful searching features using more uniform entries provided using methods of the current invention.

BRIEF DESCRIPTION OF THE DRAWINGS

FIGS. 2A–2C show the menu system, summary viewer, and graphical interface tool elements of the report viewer user interface provided for data entry review and navigation of the hierarchical knowledge base of FIG. 1. The figure illustrates a "left ventricle" hot spot on a graphic representation;

FIGS. 3A–3J further illustrate the use of the placeholder shortcut synchronization with the menu system in accordance with the invention;

FIGS. 5A–5C and FIGS. 6A–6C additionally illustrate the activation of macros and pop-up menus associated with hot spot display characteristics;

FIGS. 7A and 7B display standard full-width and signal-column reports respectively for displaying the report viewer narrative formats;

FIG. 8 illustrates a report generated using the methods and systems of the current invention.

FIGS. 9A–9C illustrate the user interface with an automatic mechanism for filtering detailed data to create a summary section of the generated report.

FIGS. 12A–12B illustrate the use of the report viewer having an embedded mini structure and allowing for selection from the report viewer;

FIGS. 14A–14C illustrate a sequential series of views in a preferred embodiment in which a menu system is embedded in a summary viewer section;

FIGS. 15A–15C illustrate a sequential series of views in a preferred embodiment in which a summary viewer system is embedded within a menu system;

FIGS. 16A–16B illustrate a sequential series of a preferred embodiment in which findings are embedded in the menu system;

FIG. 18 is an XML representation for the "Left ventricle" subtree illustrated in FIG. 16B; and FIG. 19 shows an application for constructing queries using the menu system according to a preferred embodiment of the current invention.

DETAILED DESCRIPTION OF THE PREFERRED EMBODIMENT

In presenting a detailed description of the preferred embodiment of the invention, examples are used that are based on a very simple clinical database. These examples are provided to illustrate certain elements of the invention. They are not to be construed as limiting the invention in any way.

The current invention provides methods, systems and interfaces that facilitate both the entry of medical data into a medical information database and the generation of medical reports from the medical data. The methods, systems and interfaces of the current invention typically generate a digital output that is used to populate the medical database using automated methods. Additionally, the methods, systems, and interfaces of the current invention generate a medical report that appears similar, preferably identical, to traditional medical reports.

Figure 1:
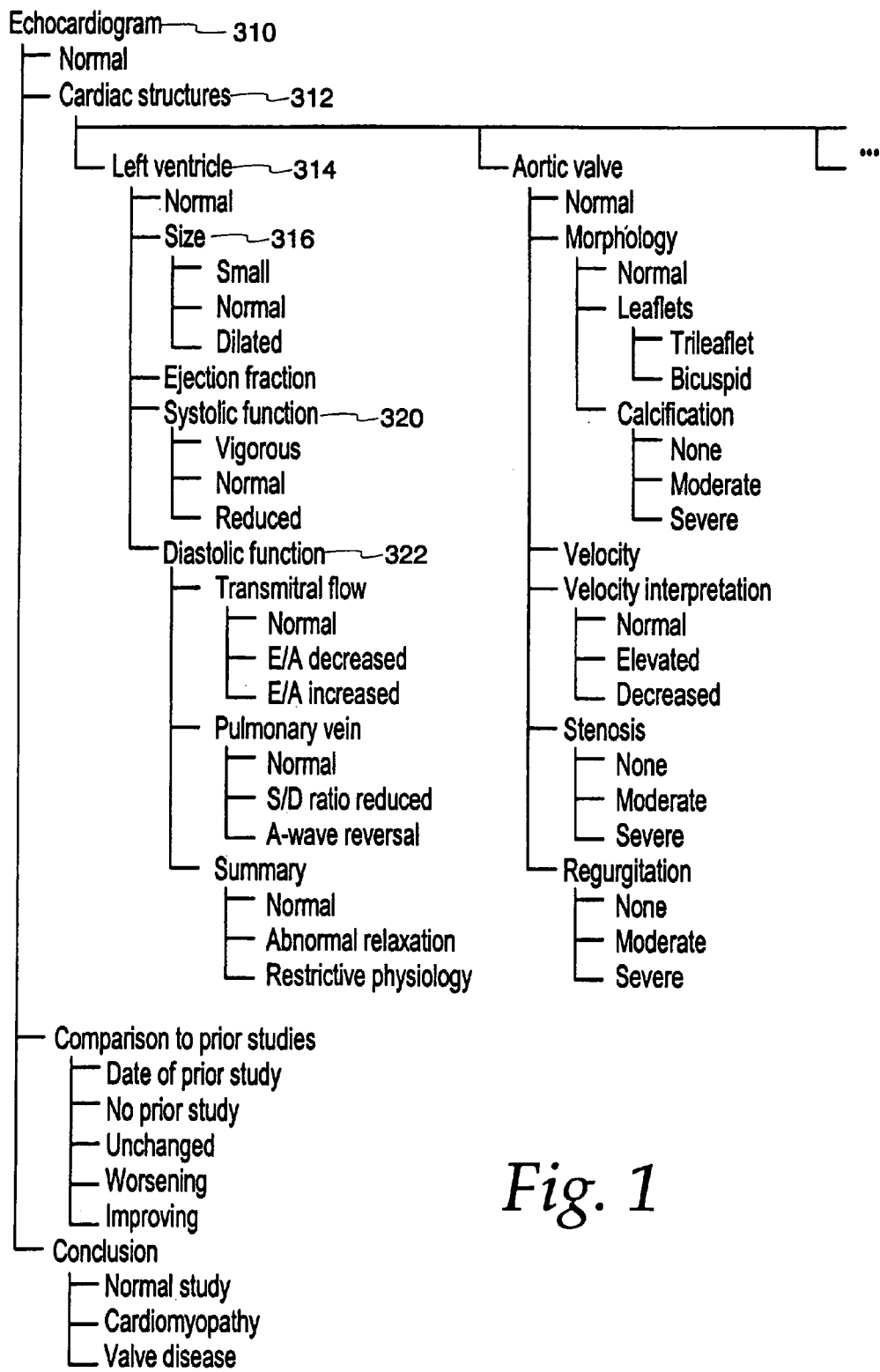
FIG. 1 provides a tree structure illustrating the hierarchical knowledge base in accordance with a preferred embodiment of the invention.

FIG. 1 shows a hierarchically-organized database view, we will refer to this view as a "knowledge base." Consistent with the accepted terminology in the field, the knowledge base may be referred to herein, as a tree, the topmost node in the hierarchy, as the root node, the path from the root node to any other node, as a branch, and a subset of the hierarchy that is itself a hierarchy, as a subtree. Each leaf node in the knowledge base hierarchy represents an atomic data item. Each branch node represents either the root of a collection of related data items, or a navigational cue leading to data items (atomic or collected) situated below it in the hierarchy.

The exemplary structure shown in FIG. 1 provides the echocardiogram aspects of the knowledge base (KB) being broken down as between normal, cardiac structures, comparison to prior studies, and conclusions which are further segmented into data fields of the database associated with the hierarchical knowledge base as discussed further below.

According to a preferred method and system for navigating the hierarchical knowledge base, navigation and data entry is provided with views supported by core elements of a user interface. The user interface facilitates direct visual cues using shortcuts and macros, as described in further detail below, for the initiation of menu-based prompts facilitating knowledge-driven data entry. For ease of reference in connection with the discussion of FIGS. 1–2, reference numerals 310–322 illustrate corresponding structures within the knowledge base such that the sample hierarchical knowledge base of FIG. 1, progressing through the data tree, illustrates electrocardiogram 310, cardiac structures 312, left ventricle 314, which includes parameters such as size 316, ejection fraction 318, systolic function 320, and diastolic function 322.

FIGS. 2A–2C show the menu system, summary viewer, and graphical interface tool elements, respectively, of the report viewer user interface provided for data entry, review, and navigation of the hierarchical knowledge base of FIG. 1. The knowledge base hierarchy is typically organized according to anatomical structures, with detailed description of those structures organized into individual subtrees. The organization may vary depending on the medical discipline or modality being represented. Electrophysiology may be organized according to measurements while other procedures such as catheterization may be organized according to anatomy. Thus, the menu system is not limited to a particular organizational structure. Navigation for data entry is done by finding each structure of interest in the menu system or summary viewer, developed as a preferred graphical mechanism for navigation of the knowledge base hierarchy.

With reference to FIG. 2A, a menu system 300 which is generally employed in the hierarchical knowledge base is illustrated which uses menu-based prompts 304, 306, 308 to facilitate data entry, for example by recording findings 302, triggering equations, and triggering macros, and for local navigation within the knowledge base. A summary viewer 324 is shown in FIG. 2B, which is used to review recorded data and for "global" navigation of the knowledge base via the finding group headings, shortcuts 321, 323, and recorded findings, which may also function as shortcuts. In FIG. 2C, a graphical interface tool 326 illustrates that the user can select "hot spots" for "global" navigation and data entry by triggering macros.

Using the described menu system 300, the user may, for example, select a menu item labeled "Echo," then "Cardiac structures," and then click on a menu item representing a regional function, e.g., the left ventricle 314. Upon selection of a menu item, the menu system 300 of FIG. 2A is then synchronized to the summary viewer 324 of FIG. 2B. The structure in the summary viewer 324 reflects the structure in the menu system 300 since it is used to shortcut into the menu system 300, as described below. Therefore, the structure of the summary viewer 324 is in large part dictated by the structure of the menu system 300. Information structure in the summary viewer is thus tied directly to information structure in the menu system 300, with the ability to record information in one place and show it in many places.

Typically, there are several types of nodes for entry using the menu system: (1) statement nodes which contain a complete statements as their contents, which users select to record the proper value; (2) text or numeric entry forms that allow a user to enter a particular value for that node; and (3) combination dialogue boxes that provide either leaf nodes that allow selection of a value for that node from a list of values (e.g., see dynamic data mapping section below), or nodes that allow a user to pick from a list of leaf, date, and time entry nodes.

Shortcuts 321, 323 in the summary viewer 324 may be used to quickly navigate into the knowledge base. As exemplified in FIG. 2B, shortcuts 321, 323 may be differentiated from other text in the summary viewer, for example by using text strings such as "<<." Shortcuts allow the user to navigate quickly to frequently-used nodes (or areas in the knowledge base tree that the user may want to have a reminder to always go to enter data) in the knowledge base tree, whereas the menu system is typically exhaustive, i.e., containing all of the data elements and clinical content needed for any kind of report. The summary viewer contains text-based shortcuts that point to specific nodes in the knowledge base hierarchy. Shortcuts serve two functions:

1) they act as hot keys into the menu system by causing the menu to open to a specified level (node) when the placeholder is selected; and
2) they are a prompt to the user for entry of data that is often required for a specific report, that is, they can serve as "placeholders" for expected data.

Placeholders and visual cues enhance shortcuts to support the placeholder state. The placeholder is a shortcut that is required for a particular user group. To this end, the host machine will have the ability to check for active (unsatisfied) placeholders. These placeholders will be marked differently than a shortcut. Placeholders thus provide shortcuts to subtrees in which information must be recorded.

The system supports two types of placeholders, as follows:

1) Unconditional Placeholders: Finding Group (FG) and shortcut within it are both marked as placeholders. These placeholders are active throughout the course of the study. E.g., Use Case: "LV Regional Function" should always be recorded for every echo study.
2) Conditional Placeholders: Finding Group (FG) is not marked as placeholder, but shortcut within it is. Conditional placeholders only become "active" whenever a finding is recorded in their FG. These conditional placeholders remain active until a finding is recorded that satisfies it. E.g., Use Case: A summary statement should be recorded whenever an intervention is recorded.

Placeholders pertain to both Entry and Review mode of the Summary Viewer using the following icons to demarcate placeholders:

A finding has been recorded in the FG and there are not active placeholders left FG contains an active placeholder (it may or may not contain findings) The following chart demonstrates the application of the icons:

|  | No recorded findings | Recorded findings |
| --- | --- | --- |
| FG is a placeholder<br>Placeholders in FG<br>(unconditional) | ! Left ventricle<br><< Size<br>! Wall thickness<br>! Regional function | ! Left ventricle<br><<Size<br>Thickness 123 mm<br>! Regional function<br>☐ Left ventricle<br><< Size<br>Thickness 123 mm<br>No RWMA |
| FG is not a placeholder<br>Placeholder in FG<br>(conditional) | First Intervention<br>! Summary<br><< Set-up<br><< Complications | ! First Intervention<br>! Summary<br><< Set-up:<br>J1234 catheter . . .<br><< Complications<br>☐ First Intervention<br>55% mid LAD<br>Set-up: J1234<br>catheter . . .<br><< Complications |
| FG is a placeholder<br>No placeholders in FG<br>Finding Group geared<br>specifically for tech.<br>A user with a limited,<br>defined set of fields. | ! Left ventricle<br><< Size<br><< Wall thickness<br><< Regional function | ☐ Left ventricle<br><< Size<br>Thickness 123 mm<br><< Regional function |
| FG is not a placeholder<br>No placeholders in FG | LV gram<br><< Global LV function<br><< Regional LV function<br><< ASD | ☐ LV gram<br>Normal LV function<br><< Regional<br>LV function<br><< ASD |

When data from a subtree defined by a placeholder node is entered, the placeholder is removed from the summary viewer and replaced with the specific patient data.

Figure 3A:
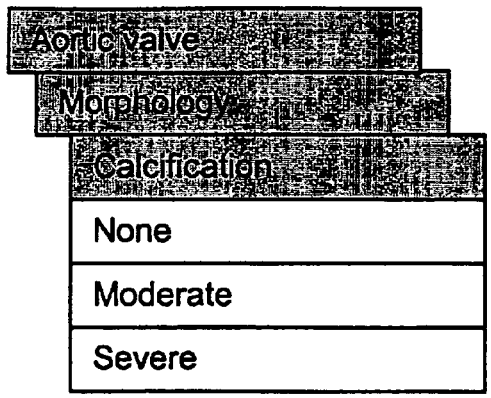
Figure 3B:
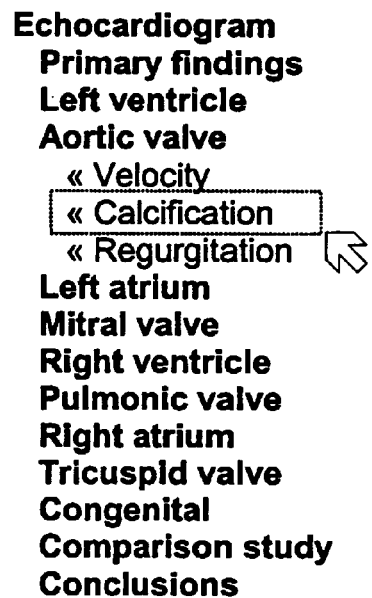
Figure 3C:
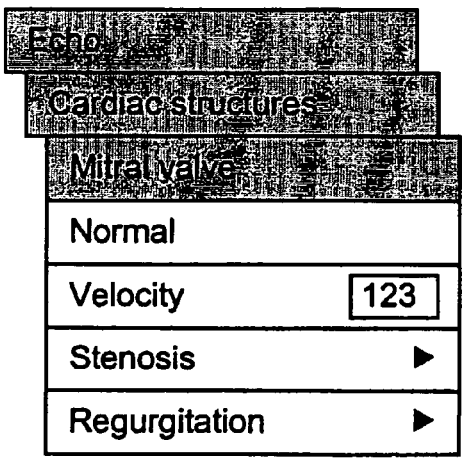
Figure 3D:
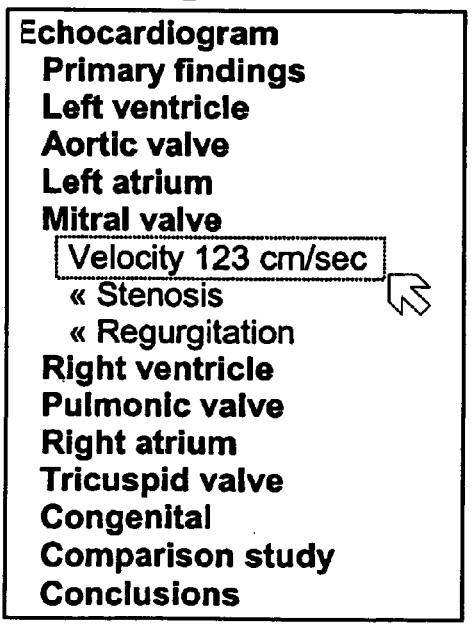

FIGS. 3A–3H illustrate the use of the shortcut synchronization with the menu system according to the described embodiment. Herein, selection of a shortcut synchronizes the menu system to the corresponding node within the knowledge base hierarchy, as shown in FIGS. 3A–3B. In FIGS. 3C–3D, selecting a recorded finding may also synchronize the menu system. FIGS. 3E–3H illustrate the view updating as a result of a finding being recorded by the menu system. In this example, the summary viewer adds a shortcuts for "Systolic function" as a result of the recording of the finding "Ejection fraction: 45%," thereby signaling the user that more information is expected (or required).

As illustrated in FIGS. 3I–3J, findings displayed in the report viewer feature may also function as shortcuts, as described below. In this case, selecting the sentence derived from a finding (in the report viewer) synchronizes the menu system to the corresponding node within the knowledge base hierarchy.

Shortcuts are prompts for common data. Therefore, when a user selects a node, the menu system typically has more categories than the summary viewer has shortcuts. The user visually may look at the shortcuts for main prompts to make comments on the most important and common information. It will be appreciated that all placeholders are shortcuts, but not all shortcuts are placeholders. Place-holders are shortcuts that are required by the user to fill in, while shortcuts are simply common or suggested areas for a user to go and fill in.

Static shortcuts and placeholders are populated from the knowledge base at the time a blank report is initiated, and are not dependent on specific patient data (other than disappearing when subtree data is entered, as noted above). Conditional or "dynamic" shortcuts that are contingent on conditions within the existing patient data, may also be employed. For example, the specific shortcuts displayed in the user interface may depend on the specific type of user (e.g., physicians, technicians, fellows, nurses, administrators, and the like), previously recorded findings, or the specific type of procedure being documented. Dynamic and/or conditional shortcuts may be provided for a variety of functions, including the following conceptual situations:

1) If a shortcuts is selected in the summary viewer, display a new set of shortcuts.
2) If a specified data element is entered, display a specified shortcut (or set of shortcuts).
3) If a specified numeric data element is within a delineated range, display a specified shortcut (or set of shortcuts).
4) If any data element is entered within the subtree defined by a specified node, display a specified shortcuts (or set of shortcuts).

In addition to shortcut-driven application behaviors, other types of knowledge-driven application behaviors may be employed. For example, a user alert feature may be employed in situations where nodes A and B are logically inconsistent (rather than completely mutually exclusive).

The graphical navigator 326 of FIG. 2C is a visual display of related anatomic structures (or any other set of related objects), that allows the user to navigate by selecting hot spots 332 on the graphic that are linked to the knowledge base hierarchy either directly (to a node or subtree) or indirectly via macros. This approach has several complimentary advantages over navigation in the menu system or summary viewer. Firstly, direct visual cues from the graphical display of familiar diagrams are provided to facilitate a convenient user-interface. Secondly, the graphical navigator 326 provides a more compact representation of cues than can be accomplished using shortcuts, with a larger number of possible cues than can be displayed at one time in the menu system.

Figure 4:
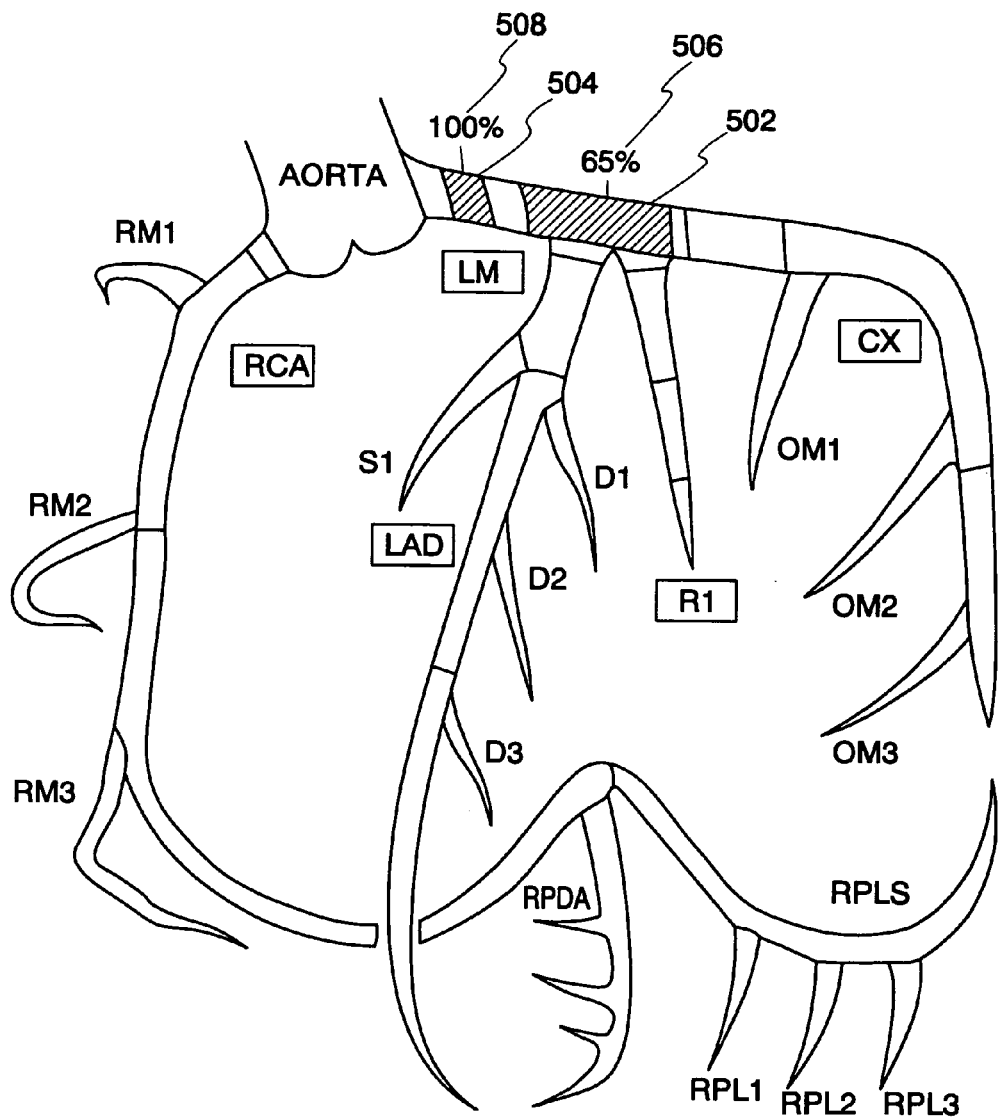
FIG. 4 illustrates an interactive graphic representation of a graphical navigator according to a preferred embodiment of the invention.

In certain preferred embodiments, as exemplified by FIG. 4, the graphic representation in the graphical navigator 326 is three-dimensional and/or inter-active. When a user records findings using an interactive graphic representation, it is updated to represent the recorded findings, thereby allowing the user to visualize their entries within the graphic representation. Recorded findings may be included within the graphic representation in many ways. For example, as shown in FIG. 4, a segment 502, 504 pertaining to a recorded finding may be highlighted, for example, with a different gray shading or with a different color, and a small note 506, 508 containing the recorded finding may be included near the marked segment. In a non-limiting alternative embodiment, the graphic representation itself could change in response to the recorded finding. For example, if a stent or catheter in a vessel is recorded, the graphic may be changed to illustrate the stent or catheter within the vessel.

Preferably, the systems and method of the current invention include macros. Macros provide a mechanism for grouping multiple, simultaneous application events into a single user action. The most common use is to trigger entry of multiple findings from the firing of a dedicated macro (e.g., using a "Non-recordable trigger node" within the knowledge base hierarchy to record a predefined set of findings), or to synchronize the interface elements (i.e., menu, viewer, etc.) to a common state (e.g., as shown in FIGS. 5–6, by clicking the hot spot 332 on a graphic). Macros provide the ability to package a complete set of actions together into one unit so that they are invoked as a unit. The entire group of information is thus packaged and made into a macro which provides for a triggerable activity off of the menu system 300, summary viewer, or graphic.

The ability to package a complete set of findings together into one unit is very useful for routine procedures. For example, a physician may record the same set of findings for certain procedures. According to preferred embodiments of the current invention, the physician may create a customized macro, which auto-matically enters the findings into a report when it is selected. This feature is referred to herein as "QUICK REPORTS." After certain findings are automatically entered using the QUICK REPORT feature, the physician may edit recorded findings based on findings of the current study.

Triggering of macros from the graphical navigator also allows for an approach to data entry that is in some ways orthogonal to the data representation in the knowledge base hierarchy. As shown in FIGS. 5–6 rather than navigating from object to object in the menu system or from placeholders, and then describing object attributes, the user is able to set a "state", or common attribute that can then be triggered for multiple objects on the graphical display. This allows multiple nodes arranged anatomically in the knowledge base to be accessed as though they were arranged functionally.

Turning again to the graphic interface with reference to FIGS. 2A–2C, "hot spots" 332 on a diagram can be used as shortcuts. Clicking the "Left ventricle" hot spot 332 synchronizes the menu system to the corresponding node within the knowledge base hierarchy and opens the associated finding group in the summary viewer. This may be implemented using an HTML page, for non-limiting example.

Figures 5A, 5B, 5C:
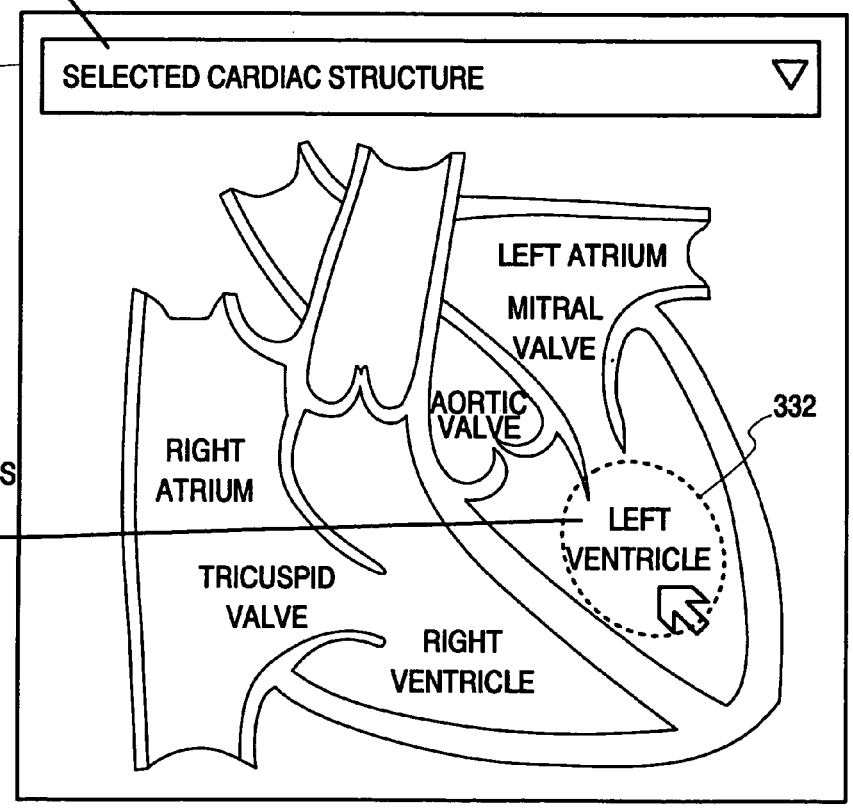
Figures 10A, 10B, 10C, 10D, 10E:
FIGS. 10A–10E provide for the embedding of the menu system within the elements of the user interface.

These "hot spots" which may also be used to record findings are illustrated more particularly on the diagrams of FIGS. 5A–5C. For example, as shown in FIG. 5C, clicking the "Left ventricle" hot spot will cause the Left ventricle's "Is normal" macro to be initiated. This macro, for example, may include five "normal" findings as shown in FIG. 5B.

With reference to FIGS. 6A–6C, and particularly FIG. 6C, clicking "Left ventricle" hot spot may display a "macro" pop-up menu containing the following macros, for example:
1) "Is normal": Record 5 LV normal findings.
2) "Is essentially normal": Record 5 LV normal findings and synch to LV node.
3) "Describe structure": Synch to LV node.

The contents of the pop-up menu may be context-sensitive or, alternatively, may be dynamic, as discussed above.

In certain preferred embodiments, the systems and method of the current invention include dynamic data mapping. In dynamic data mapping, a user has the ability to customize menus so that specific items may be selected from lists of items that are maintained separately from the knowledge base, e.g., lists with contents that change frequently or are generated based on user actions during the medical procedure. For example, the list of items may be based on an institution's inventory of the equipment used in a type of medical procedure or the inventory items that were actually used during a specific (individual) procedure. Preferably, the specific items listed are those that are typically used by a user, rather than an exhaustive list of all possible specific items. More preferably, the specific items listed are those that are in an inventory of a user's institution. Most preferably, the specific items listed are those that were actually used during a specific (individual) procedure. In this case, the contents of the dynamically-mapped list are generated automatically by linking nodes in the hierarchical knowledge base described above, with elements in the institution's inventory database (e.g., a particular manufacturer's name, product number, and lots for medical devices). In certain preferred embodiments, the customized lists are created by the selection of certain items from a short list of items drawn from an inventory system, without modifying the knowledge base hierarchy.

The dynamically-mapped items are presented within the menu interface so that a physician can describe how these items were used during the procedure (i.e., the physician records information from the hierarchical knowledge base together with information dynamically-mapped from an external database to form a complete narrative description of the procedure). The integration within the interface is seamless; in fact, the user is largely unaware that the dynamically-mapped information originates from an external source.

An example of a sentence created in a medical report using dynamic data mapping during data entry is shown in FIG. 8. In the section Vascular Interventions, the equipment identifier "SciMed Wiseguid 6Fr AL 1 FX guiding catheter" 470 was retrieved from an external database using Dynamic Data Mapping. In preferred embodiments, this particular catheter is a selectable item from a "Guiding Catheter" list because it is entered into the host system's inventory subsystem based on the typical, or preferably the current inventory of the host institution or the devices used during the current procedure. The system typically then develops a coherent narrative based on the selection.

Dynamic data mapping is used when the host system receives information (e.g., measurements, free text, etc.) from another device (e.g., an ultrasound machine, CT, ECG, etc.) and does not have an exact place to put it in the menu system. For example, a technician performing an obstetrics ultrasound examination would have taken several measurements, BPD, HC, FL, etc. These measurements would be passed from the ultrasound machine to the host system computer. The host system may not be able to truly resolve what the measurements are but could at least understand that they are measurements. The menu system would have the BPD measurement node dynamically mapped, such that when the user went to this node, the user would be presented with all of the measurements taken (BDP, HC, FL, etc.). From there, the user can pick from the list.

In addition to the data entry interface, preferred embodiments of the current invention provide a report generating function that automatically generates a set of reports from information entered in the data entry functions of the program. Most preferably the reports are medical reports that are formatted to visually appear similar or identical to reports generated by other methods and systems. For example, reports typically include a Summary section and a Demographics section. Other sections of a report may be included in the report. Additionally, a user may define a different name for the Summary and/or Demographics sections of a report. FIGS. 7A and 7B display Summary sections of standard full-width and single-column reports respectively for displaying the report viewer narrative formats. Herein, the report viewer formats 328, 330 display the narrative report derived from the recorded findings, which may further be displayed as a standard full-width report (above) to give the physician a WYSIWYG view of the report, or as a single-column report (left) that can share screen real estate with other data (images, for instance). In certain preferred embodiments placeholders, as described above, are included in a report. These placeholders when selected, cause the menu system to synchronize to the node in the knowledge base represented by the placeholder.

The report sections feature separates data organization used in the knowledge base from the organization of the information in the report. Typically, every finding in the knowledge base is associated with one or more report sections. Therefore, information may be tagged for its location within a report, in addition to its location within the database hierarchy. The knowledge base defines the sections that are available for the report, and then defines the sections for the data. In preferred embodiments, XML (extensible markup language) is used for tagging data entered by a user. The data contained in XML is preferably formatted using XSL (extensible style language). This allows data that is displayed by tree path order and grouped into finding groups in the summary viewer to be displayed in any arbitrary layout within the report. It also allows data to be displayed in multiple sections or subsections within the report.

FIGS. 8 and 9 provide additional examples of report generated using the methods of the current invention. The contents of the summary section are elements that come from the study as a whole, i.e., aggregated together and presented in a summary section in the report which comprise the part of the report that the referring physician reads first.

The Summary section contains Information entered into nodes marked primary. In certain embodiments, as indicated in FIG. 9, the Summary section includes a separate section of Primary findings. Findings may be selected or deselected as primary by a user, for example, by selecting the finding and clicking on a designated "Primary" button. A user, for example a physician, may set a finding to primary to bring special attention to the finding. Alternatively, findings may be selected as primary automatically by an autoprimary feature, as described below. Furthermore, findings may be conditionally marked as autoprimary. For example, if data from node A is present or has a value within a specified range, then node B becomes autoprimary.

Report sections can be by definition nested with sections and subsections defined. Data from the knowledge base can be directed into any particular report section and subsection, or into multiple report sections and subsections. In preferred embodiments, report-generating functions are flexible and user-customizable. Therefore, users can aggregate information according to their preferences.

Certain preferred embodiments of the current invention include an autoprimary feature. The autoprimary feature automatically filters detailed data to create the Summary section of the report based on predefined or user-defined rules. For example, as shown in FIG. 9, "Normal LV size" is marked as "auto primary". Auto primary is an attribute of an individual node. In certain embodiments, the autoprimary attribute is static (always occurs for instances of the node). Every time data is entered for an autoprimary node, the data is provided as a summary statement. An autoprimary designation may be conditional, (e.g., if the user indicates mildly calcified, and then a statement B, the mildly calcified finding may become a primary or summary finding because of statement B. Accordingly, such knowledge driven data entry or knowledge driven behaviors may be associated pieces of the subtree or knowledge base with respect to other application behaviors based on specific patient data that is being entered.

In addition, the auto-primary may be provided with a conditional mechanism for findings included in the Primary Findings Summary automatically, without user intervention. Often, the importance of a numerical finding depends on whether it is abnormal. Conditional auto-primary is the inclusion of a numerical test prior to listing a finding as primary or not. In cardiac catheterization, for example, if the stenosis lesion percentage is greater than 70%, it makes sense in this field to include it as a primary finding. If it is less than 70%, on the other hand, it is better to omit it from the primary findings list. While users will still be able to manually edit the primary finding status, reasonable initial tests should greatly reduce the time physicians spend manually adjusting the primary findings. At the time of numerical data entry the value entered or selected should, subject to a numerical logic test (e.g., >70%) be set as primary. Edits that do not change the value should not trigger reevaluation of the auto-primary test.

The described menu system 300 supports the ability to automatically primary a finding based on its value meeting certain conditions predetermined for that node. The following list the set of possible conditions that may be predetermined for a given node:

>x value of recorded finding greater than x
>=x value of recorded finding greater than or equal to x
<x value of recorded finding less than x
<=x value of recorded finding less than or equal to x
[x,y] value of recorded finding greater than or equal to x and less than or equal to y (inclusive)

Certain preferred embodiments include rank ordering of findings marked as primary by an autoprimary feature, described below, to allow ordering of the primary findings in the summary report by a user. In other words, the auto primary function may not be a binary +/− (equal weighting), but rather may be assigned score (e.g., 0–5). This allows decision logic to determine not only whether findings should be included in the summary section, but also the order (or prominence) in which findings should be displayed.

In addition to the embodiments described herein wherein the report viewer user interface displayed menu, graphic display, and summary viewer sections separately on a screen, the current invention provides alternative embodiments wherein one or more of these sections are embedded within each other. FIGS. 10A–10E provide examples of preferred embodiments of the current invention wherein the menu system is embedded within other elements of a preferred user interface. These embodiments more efficiently use available area of a display, and provide a user with a very efficient method for moving from the summary viewer to the menu system. These embodiments take advantage of the fact that the distinction between the menu system and the summary viewer in the current invention is arbitrary. In one preferred embodiment described in more detail below, one or more placeholders in the summary viewer appear in the menu system within the viewer proper. In another preferred embodiment illustrated in FIGS. 10A–10E, menu items are embedded within placeholders in the summary viewer.

Figure 11A:
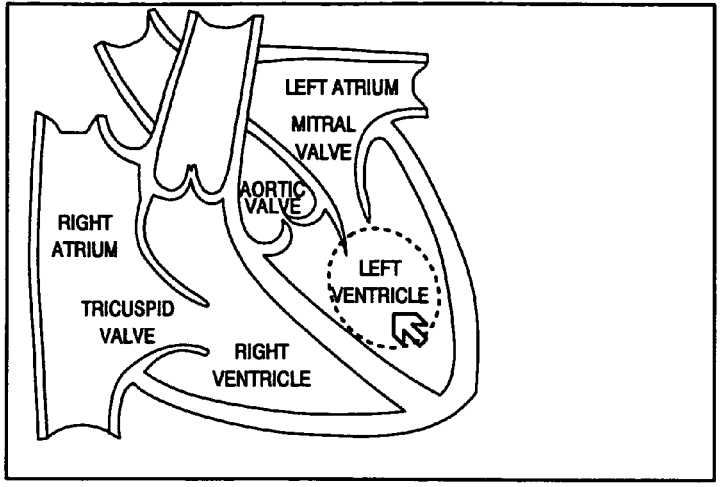
FIGS. 11A–11C combine the hot spot, pop-up menu, and shortcut structures in the graphical user interface.
Figure 11B:
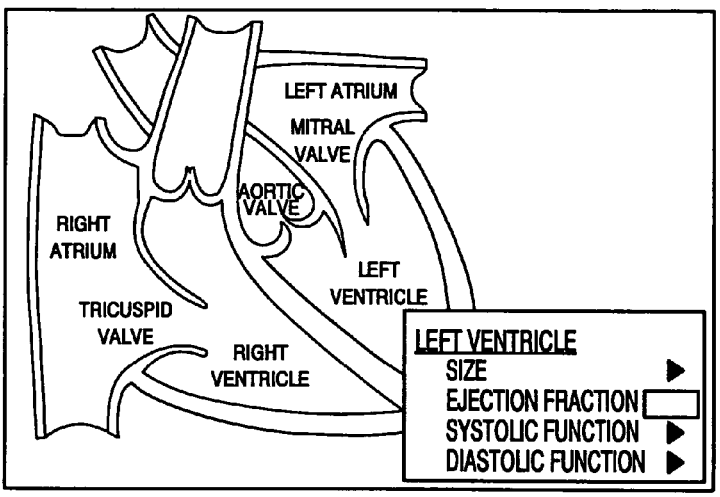
Figure 11C:
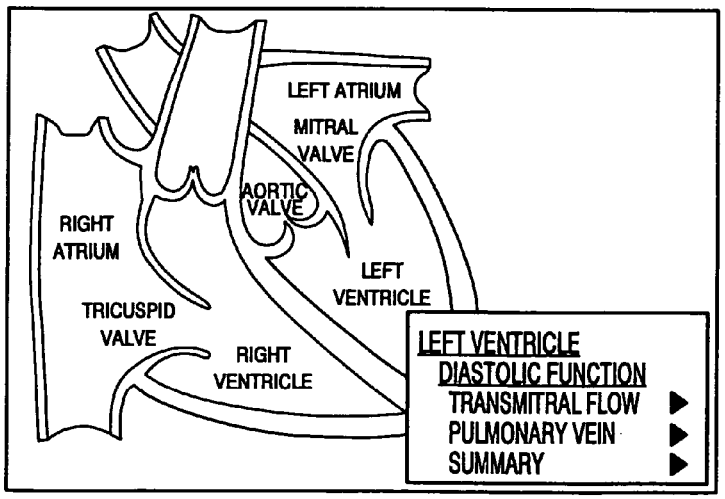

FIGS. 11A–11C show preferred embodiments which combine the hot spot, pop-up menu, and shortcut structures in the graphical user interface. The menu and/or summary functions may be combined in the graphic interface. In these embodiments, selecting a "hot spot" on the graphic causes the menu system to roll out within the graphical interface. Additionally, FIGS. 12A and 12B illustrate the use of the report viewer having an embedded menu structure and allowing for selection from the report viewer.

Figure 13:
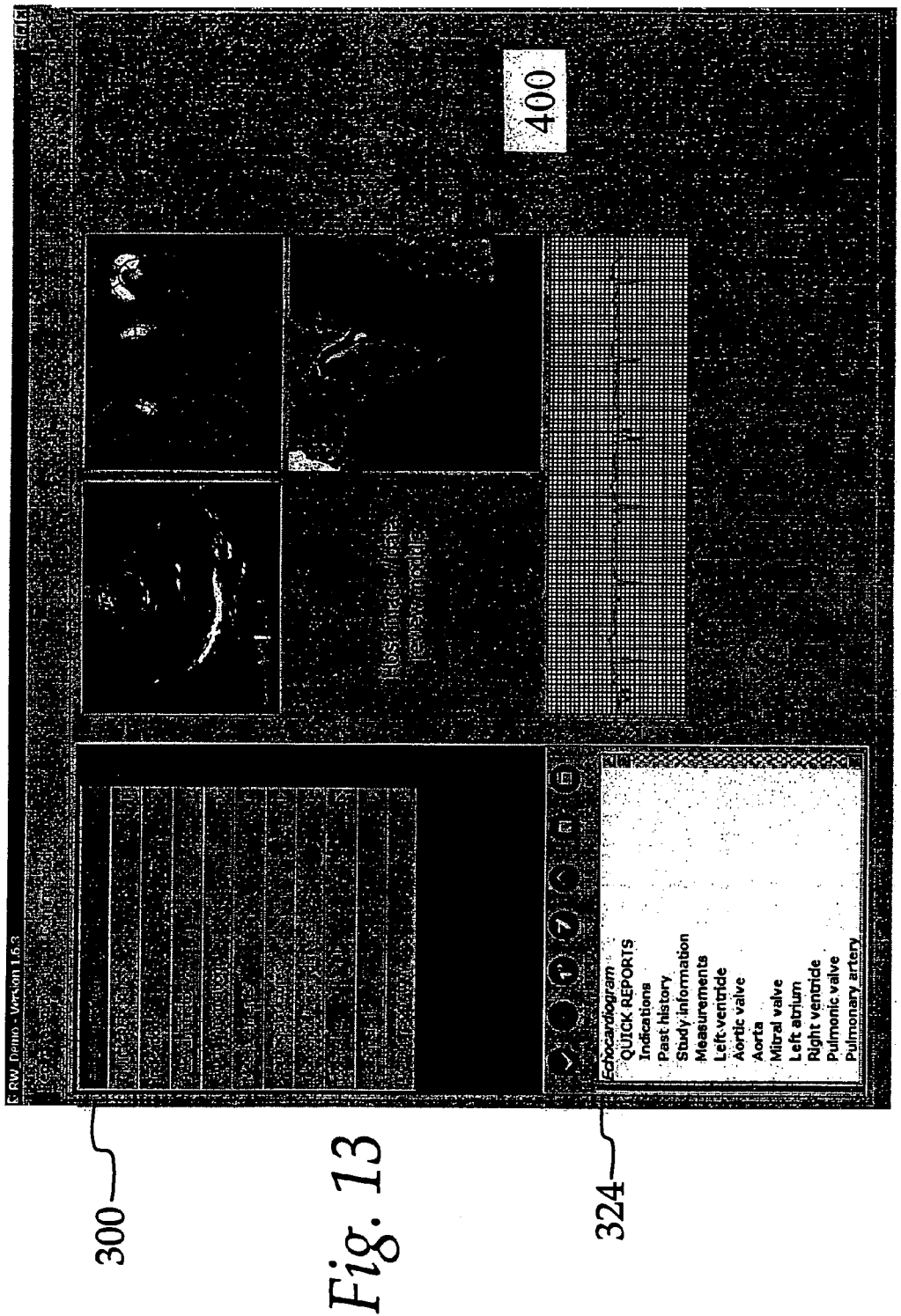
FIG. 13 illustrates a user interface a menu system, a summary viewer, and an images section, according to a preferred embodiment of the current invention.

FIG. 13 shows a variation of the preferred user interface wherein a menu 300 is displayed above a summary viewer 324 which together appear in a left portion of the user interface. On the right portion of the user interface, one or more images 400, which assist in entering data, are provided. Most preferably these images are images from medical procedures.

Figure 14B:
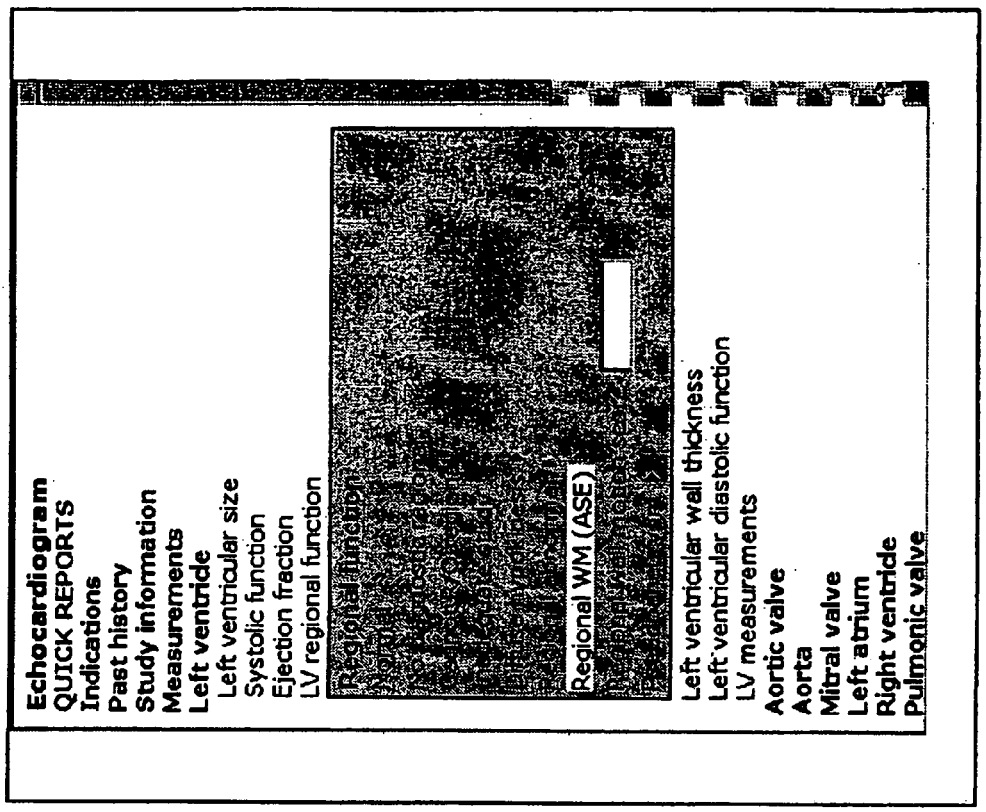
Figure 14A:
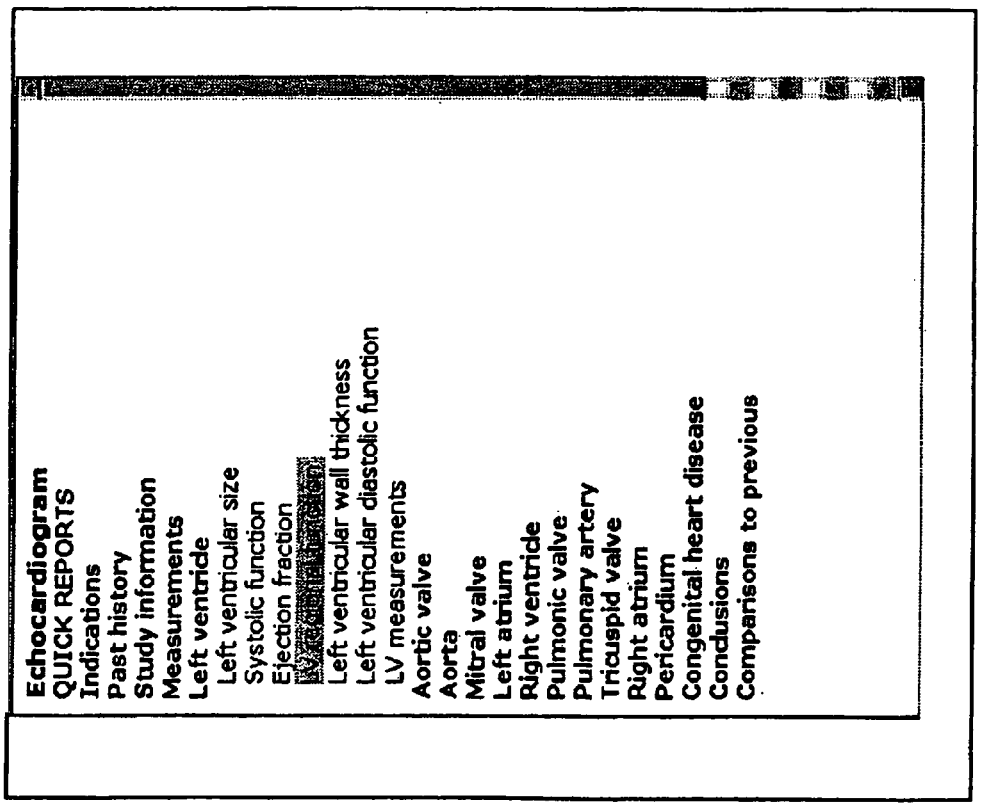
Figure 14C:
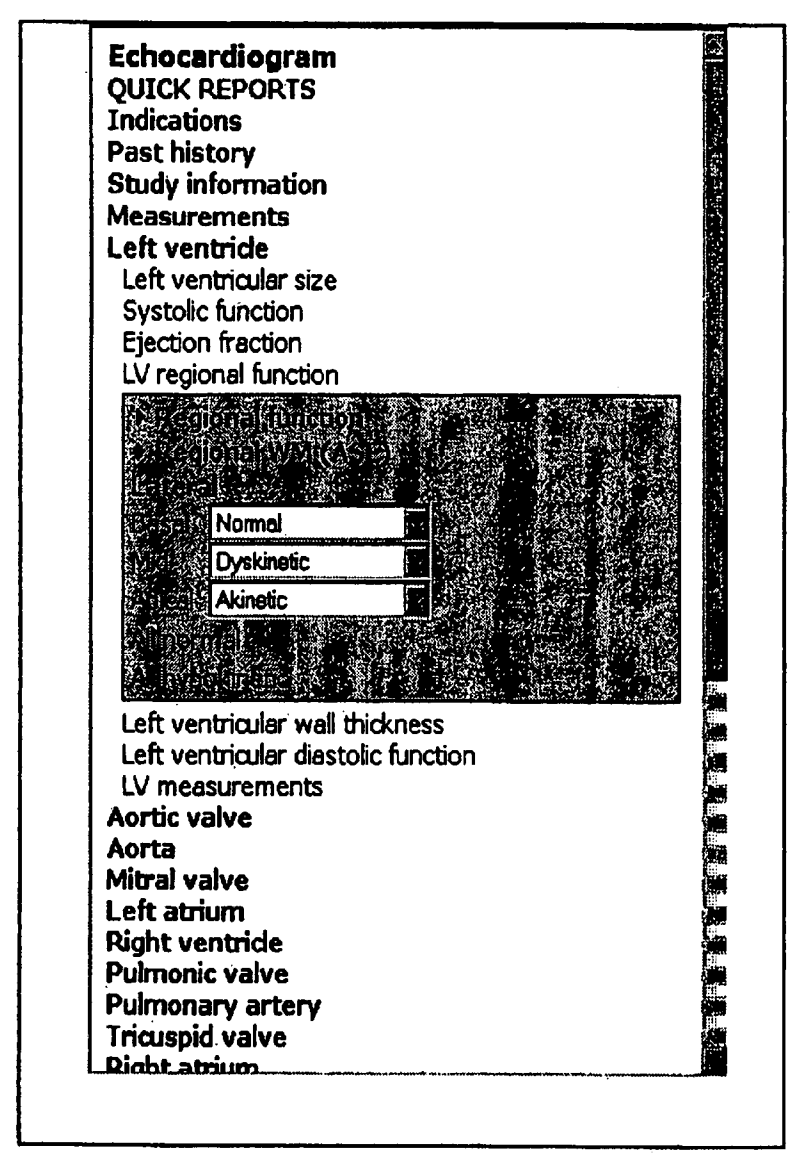

Referring now to FIGS. 14A–14C, reference is again made to specific embodiments in which the summary viewer and menu items are combined in a single screen area. As shown in the non-limiting example illustrated in FIG. 14, selecting the shortcut "LV regional function" (FIG. 14A) causes the menu system to be displayed below the selected shortcut (FIG. 14B). The resulting menu system is rooted at the node in the hierarchical database view corresponding to this shortcut. The user then selects items from the menu system to (1) navigate the hierarchical database view (both downwards and back upwards), and (2) record data. For example, selecting "Regional WM (ASE)" followed by "Lateral" navigates two levels further down in the menu system along the selected branch and selecting "Akinetic" from the "Apical" pick list records the corresponding finding (FIG. 14C).

While this approach preserves screen real estate by displaying the menu system (in a convenient location) only when it is actively being used, it maintains a visual and functional distinction between the menu system and the summary viewer. This distinction, in turn, requires that the user interact differently with these two components, which may not be preferred by all users.

Figure 15C:
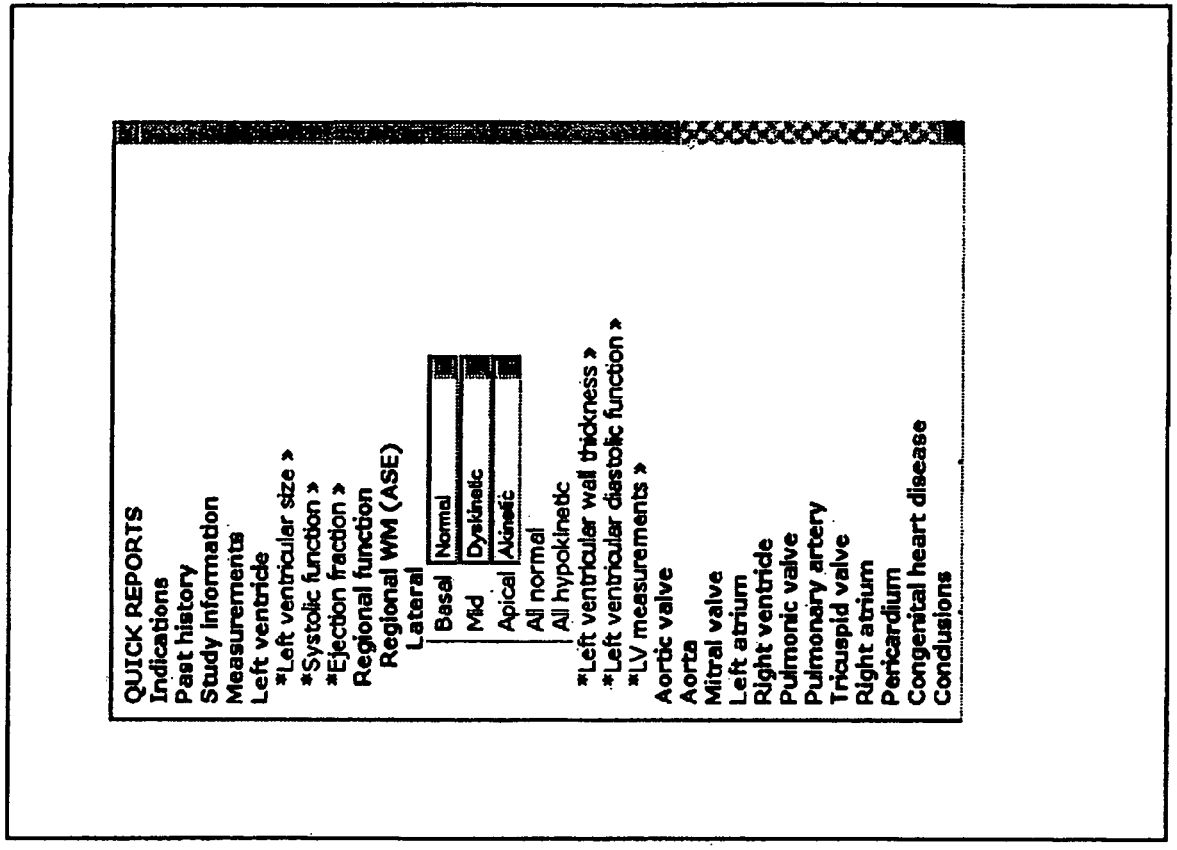

In another preferred approach, the summary viewer's placeholders and findings are displayed within the context of menu system. In FIG. 15A, for example, the level in the hierarchical database view rooted at "Left ventricle" is displayed. Selecting "Regional function", causes the level in the hierarchical database view rooted at this node to be displayed (FIG. 15B). Continuing downward by selecting "Regional WM (ASE)" and "Lateral" produces the result shown in FIG. 15C. Both the structure and the contents of the menu system are retained, including the path buttons ("Left ventricle", "Regional function", "Regional WM (ASE)", "Lateral") and the buttons for current level ("Basal", "Mid", "Apical", "All normal", "All hypokinetic"). But rather than displaying these elements in isolation, they are displayed within the context of the relevant "Left ventricle" placeholders (denoted with as asterisk in the figures above). In FIG. 15A, these placeholders overlay the current level in the menu system (and the asterisk markers are placed on the menu system buttons). In FIGS. 15B and 15C, these placeholders lie outside the structure of the hierarchical database view branch being navigated but within the "Left ventricle" subtree and are displayed as such.

This integration of menu and viewer can be extended to findings, as well. In the examples below, findings 450 are depicted in the context of the current level of the menu system. In FIG. 16A, the findings are nested below the node on the current level that is their ancestor. Having navigated downwards in FIG. 16B, the findings are displayed as being outside the current branch but inside the "Left ventricle" subtree, with the exception of "No diagnostic regional wall motion abnormalities", which is displayed as being outside the "Regional WM (ASE)" subtree but inside the "Regional WM (ASE)" subtree.

Figure 17:
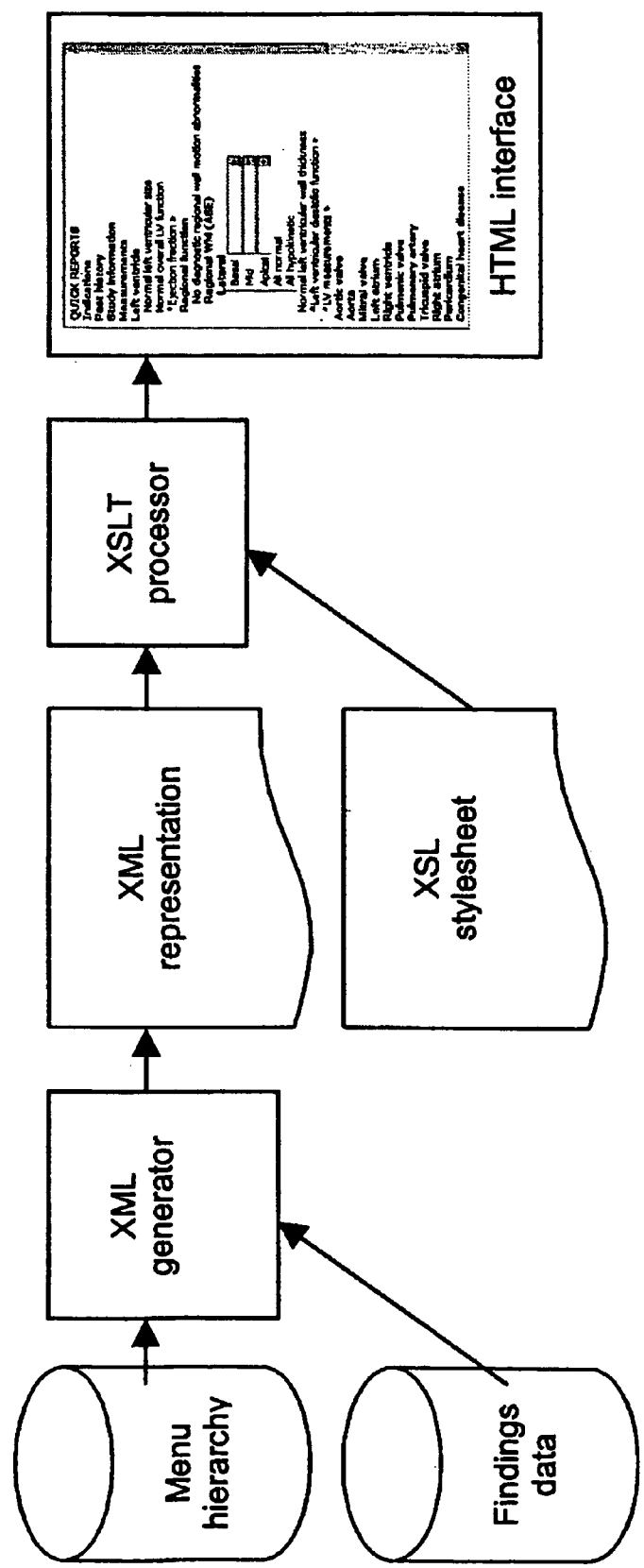
FIG. 17 is a flow chart of the steps for generating an HTML menu system and summary viewer using XML and XSLT.

Implementing the menu system and summary viewer using conventional interface technologies (e.g., a mix of forms, OCX's, and other controls) has proven to be both time-consuming and difficult to customize. An alternative is to represent the integrated menu system/summary viewer interface using HTML and to derive the HTML interface from an XML representation of the menu system/summary viewer using XSLT. The steps in this process are illustrated in FIG. 17. This process begins with the XML generator creating an XML representation of the structure and content of the menu system/summary viewer. This task requires traversing the hierarchical database view and findings data in parallel, situating findings, and placeholders in their appropriate position within the menu structure. FIG. 18, for example, shows the XML representation for the "Left ventricle" subtree illustrated in FIG. 17B. The XSLT processor then takes the XML representation and maps it to an HTML representation of the interface based on the transformational templates given in an XSL stylesheet.

The advantage of this approach is that it clearly separates the definition of the structure and content of the interface (in XML) from the definition of the interface's "look and feel" (in XSL). This, in turn, makes it possible and easy to change the interface's "look" independent of its structure.

Certain embodiments of the methods and systems of the current invention include a database searching function (i.e., querying function). In addition to supporting data entry, the menu system provides an intuitive mechanism for specifying database queries on the data recorded from a knowledge base hierarchy. In query creation mode, the user navigates through the knowledge base hierarchy by selecting items from the menu system (in much the same manner as is done during data entry). However, selecting a recordable item (e.g., a leaf node) causes the recording of a query subexpression for that data item rather than the recording of the data item itself. The resulting query expression might be an SQL SELECT statement, or a set of SQL SELECT statements, that specify rules for retrieving the data item from a relational database. Any method known for querying databases can be used with the current invention. For example, but not intended to be limiting, the query might utilize an XSL rule set that retrieves the item from an XML representation of the recorded data. An important advantage of the query construction feature of the current invention is that the user does not need to be familiar with a query language to search the database.

Figure 19:
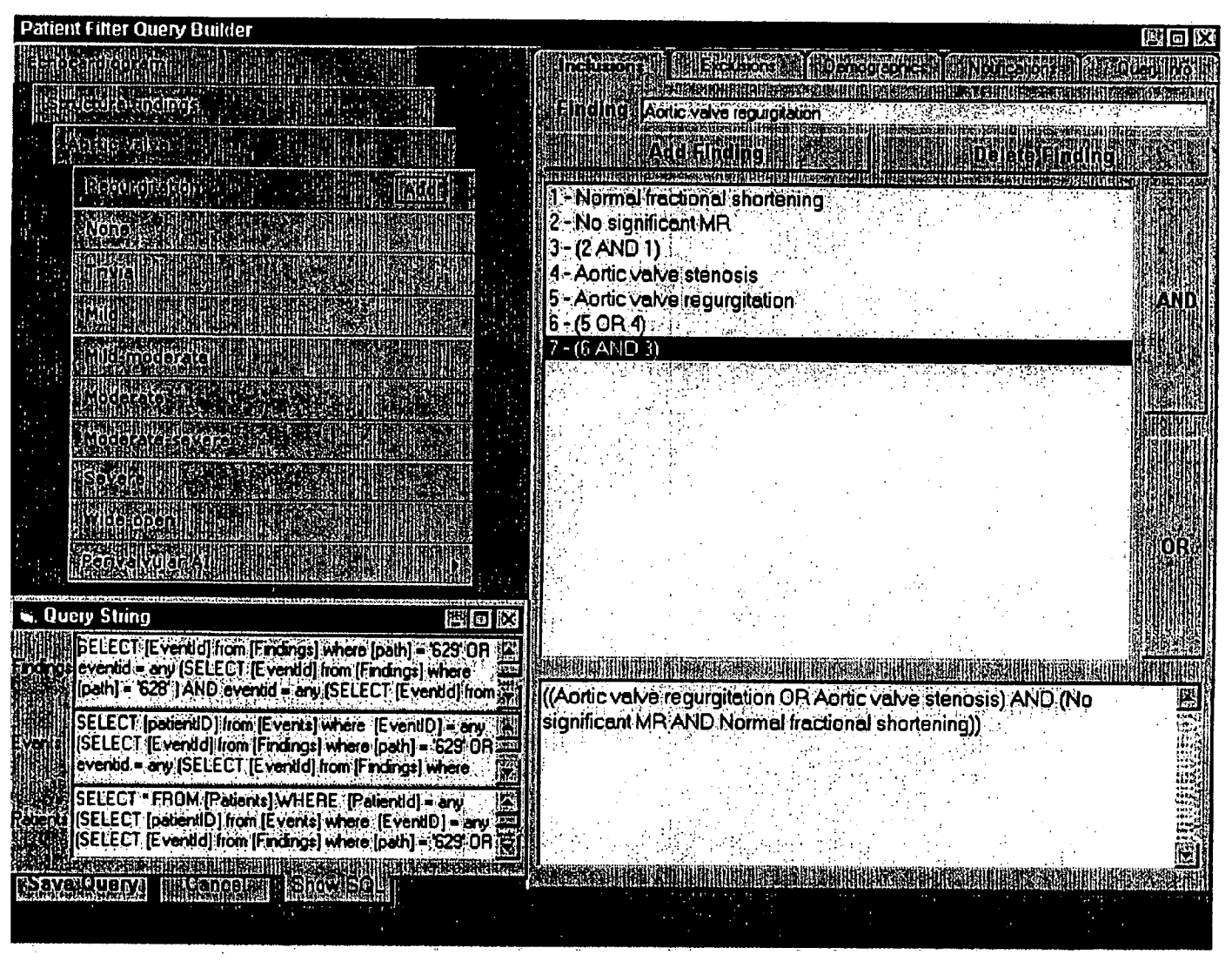

FIG. 19 shows an application for constructing queries using the menu system. The query subexpressions are selected using the cascading menu system (upper left). These elements are then combined to form more sophisticated conjunctive/disjunctive inclusion and exclusion expressions by AND'ing and OR'ing these subexpressions in a simple pair-wise manner (upper right). The resulting query is then displayed in English (lower right) or in SQL or XSL (lower left).

The foregoing disclosure of embodiments of the invention has been presented for the purpose of illustration and description. It is not intended to be exhaustive or to limit the invention to the precise forms disclosed. Many variations and modifications of the embodiments described herein will be obvious to one of ordinary skill in the art in light of the above disclosure. The scope of the invention is to be defined only by the claims appended hereto, and by their equivalents.

What is claimed is:

1. An automated method comprising:
   providing a hierarchically-organized database comprising a plurality of nodes;
   displaying:
   a first series of items that correspond to a first group of the plurality of nodes as comprise a portion of the hierarchically-organized database;
   at least one user-selectable additional item that corresponds to a specific one of the plurality of nodes that does not comprise a part of the first group of the plurality of nodes;
   upon detecting selection of the at least one user-selectable additional item, displaying a second series of items that correspond to a second group of the plurality of nodes, which second series is at least partially different than the first series;
   detecting a medical examination data entry interaction with at least a specific one of the first and second series of selectable items and entering corresponding medical examination data into storage via the hierarchically-organized database in response to such interaction to provide entered data; and
   generating an automated medical report by transferring the entered data into a report generation process.

2. The automated method of claim 1 and further comprising:
   providing a knowledge base associated with the hierarchically-organized database; and
   wherein generating an automated medical report further comprises separating information regarding organization of the knowledge base and a user interface from information corresponding to the entered data and associating the entered data with sections used to organize information in the automated medical report.

3. The automated method of claim 1 wherein displaying further comprises displaying a graphical representation of an anatomical region of a patient, the graphical representation comprising a series of user-selectable portions effective to change the series of items upon selection by a user.

4. The automated method of claim 3 wherein displaying a graphical representation further comprises displaying a graphical representation having a user-selectable region to facilitate displaying at least one additional user-selectable additional item in relation to the graphical representation to facilitate displaying a third series of items thereon, wherein the graphical representation comprises a set of user recorded data items.

5. The automated method of claim 3 wherein displaying a graphical representation further comprises altering the graphical representation to reflect a set of user recorded data items.

6. The automated method of claim 1 wherein generating an automated medical report further comprises generating an automated medical report that comprises at least one of:
   information regarding measurement tools;
   three-dimensional graphics;
   CT images;
   MR images; and
   ultrasound images.

7. The automated method of claim 1 wherein displaying a second series of items further comprises displaying the second series of items in an embedded view with the first series of items.

8. The automated method of claim 1 wherein displaying the at least one user-selectable additional item further comprises displaying the at least one user-selectable additional item within a summary viewer section, wherein the first and second series of items are displayed within a section visually separated from the summary viewer section on a user interface.

9. The automated method of claim 1 wherein displaying the at least one user-selectable additional item further comprises displaying the at least one user-selectable additional item within a summary viewer section, wherein the first and second series of items are also displayed within the summary viewer section.

10. The automated method of claim 1 wherein displaying a first series of items and displaying a second series of items further comprises displaying the first and second series of items within a first section of a user interface, and wherein displaying the at least one user-selectable additional item further comprises displaying the at least one user-selectable additional item within the first section.

11. The automated method of claim 1 wherein displaying further comprises displaying a medical image viewing area comprising a medical image of a patient related to the automated medical report.

12. The automated method of claim 1 wherein the at least one user-selectable additional item is dependent on information regarding a user, and wherein displaying further comprises displaying a series of placeholders on a user interface, these placeholders comprising prompts for required data.

13. The automated method of claim 1 and further comprising, prior to generating the automated medical report, displaying at least one additional one of the at least one user-selectable additional items based on entered data, the at least one additional one of the at least one user selectable additional items representing an additional one of the plurality of nodes in an arrangement facilitating global navigation of the hierarchically-organized database.

14. The automated method of claim 1 and further comprising selecting previously recorded data items and marking them as primary, and wherein generating the automated medical report further comprises prominently displaying the data items that are marked as primary.

15. The automated method of claim 14 wherein at least some displayed data items include an auto-primary attribute such that the recording of such data items automatically results in their being marked as primary.

16. The automated method of claim 15 wherein including an auto-primary attribute further comprises including an auto-primary attribute that is conditioned, at least in part, upon predetermined criteria regarding selective display of data when generating the automated medical report.

17. The automated method of claim 14 wherein prominently displaying the data items that are marked as primary further comprises ordering the data items that are marked as primary as a function, at least in part, of a corresponding relative importance of each of the data items.

18. The automated method of claim 1 and further comprising providing a macro capable of being initiated by a user by selecting at least one of:
   the at least one user-selectable additional item;
   one of the first and second series of items;
   a portion of a graphic representation; and
   wherein initiation of the macro causes entry of preset data into a plurality of the nodes.

19. The automated method of claim 1 and further comprising providing a query function wherein data and nodes of the hierarchically-organized database are selected by a user to construct a database query.

20. The automated method of claim 1 wherein displaying further comprises using Hypertext Markup Language code to generate such displays, and wherein the Hypertext Markup Language code is derived from an Extensible Markup Language representation using Extensible Style Language Transformation.

* * * * *